_(12)_ United States Patent
Cameron et al.

(10) Patent No.: US 9,423,635 B1
(45) Date of Patent: Aug. 23, 2016

(54) INTEGRATED MAGNETO-OPTIC MODULATOR/COMPENSATOR SYSTEM, METHODS OF MAKING, AND METHODS OF USING THE SAME

(71) Applicant: The University of Toledo, Toledo, OH (US)

(72) Inventors: Brent D. Cameron, Waterville, OH (US); Brandon W. Clarke, Stow, OH (US)

(73) Assignee: The University of Toledo, Toledo, OH (US)

( * ) Notice: Subject to any disclaimer, the term of this patent is extended or adjusted under 35 U.S.C. 154(b) by 260 days.

(21) Appl. No.: 14/169,280

(22) Filed: Jan. 31, 2014

(51) Int. Cl.
| | |
|---|---|
| *G01J 4/00* | (2006.01) |
| *A61B 5/00* | (2006.01) |
| *G02B 5/30* | (2006.01) |
| *G02F 1/09* | (2006.01) |
| *G01N 21/21* | (2006.01) |

(52) U.S. Cl.
CPC . *G02F 1/09* (2013.01); *G01N 21/21* (2013.01)

(58) Field of Classification Search
CPC ... G01N 21/21; G01N 27/3274; G01N 21/23; G01N 2021/217; G01N 2201/067; G01J 4/00
USPC .......... 356/369, 367; 600/318, 319, 336, 316, 600/322; 359/484.02
See application file for complete search history.

(56) References Cited

U.S. PATENT DOCUMENTS

| | | | |
|---|---|---|---|
| 6,246,893 B1 * | 6/2001 | Gobeli | A61B 5/14558 600/318 |
| 6,912,080 B2 | 6/2005 | Minemoto | |
| 6,958,845 B2 | 10/2005 | Hiironen et al. | |
| 6,999,808 B2 | 2/2006 | Gobeli et al. | |
| 7,133,579 B2 | 11/2006 | Elezzabi et al. | |
| 7,245,952 B2 | 7/2007 | Cameron | |
| 7,444,040 B2 | 10/2008 | Iwatsuka | |
| 8,351,117 B2 | 1/2013 | Gao | |
| 2010/0234704 A1 | 9/2010 | Cameron | |

OTHER PUBLICATIONS

Clarke: "Thesis: "Development and optimization of an integrated Faraday modulator and compensator design for continuous polarimetric glucose monitoring".", May 1, 2013, pp. 1-276.*

* cited by examiner

*Primary Examiner* — Tarifur Chowdhury
*Assistant Examiner* — Sunghee Y Gray
(74) *Attorney, Agent, or Firm* — MacMillan, Sobanski & Todd, LLC

(57) ABSTRACT

Described herein is an integrated Faraday modulator and Faraday compensator (IFMC) system. Further described are methods of making an IFMC system, methods of customizing an IFMC system for a specific application, and methods of optimizing an IFMC system for a specific application. Further described is a robust 3D Finite Element Model (FEM) for designing and optimizing an IFMC system. Further described are optical instruments comprising an integrated Faraday modulator and Faraday compensator requiring only one optical crystal.

27 Claims, 24 Drawing Sheets

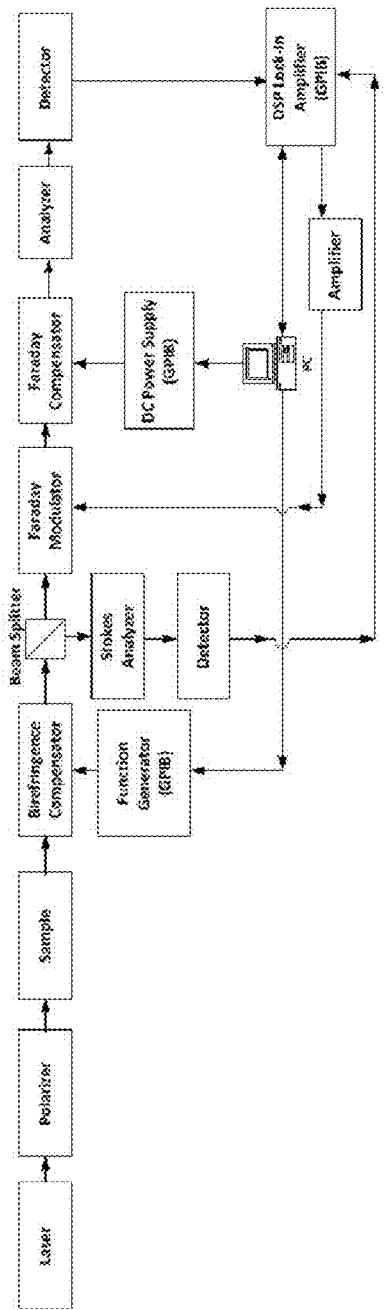
PRIOR ART FIG. 1

| Expected Inductance (mH) | Measured Inductance (mH) | Calculated Inductance (mH) | Inductance Error (%) | Measured Impedance (Ω) | Calculated Impedance (Ω) | Impedance Error (%) |
|---|---|---|---|---|---|---|
| 6.8 | 6.65 | 6.64 | 0.15 | 5.14 | 5.16 | 0.39 |
| 15 | 14.7 | 14.61 | 0.61 | 45.80 | 45.73 | 0.15 |
| 68 | 67.7 | 67.96 | 0.38 | 48.70 | 48.67 | 0.06 |
| 100 | 97.8 | 97.62 | 0.18 | 72.96 | 73.17 | 0.29 |
| 220 | 224 | 223 | 0.45 | 399 | 391 | 2.01 |
| 470 | 462 | 462 | 0 | 624 | 626 | 0.32 |

INTEGRATED MAGNETO-OPTIC MODULATOR/COMPENSATOR SYSTEM, METHODS OF MAKING, AND METHODS OF USING THE SAME

RELATED APPLICATIONS

None.

STATEMENT REGARDING FEDERALLY SPONSORED RESEARCH

This invention was made with no government support. The government has no rights in the invention.

BACKGROUND OF THE INVENTION

Diabetes is known to cause high levels of glucose to circulate in the bloodstream due to a lack of, or resistance to, the hormone known as insulin. Several studies have shown that closely monitoring blood glucose levels can significantly decrease the long-term health effects of diabetes. Though conventional methods of personalized glucose monitoring are done by extracting blood from the fingertip, more patient-friendly methods of glucose monitoring are desired. One such method involves the use of optical polarimetry.

A schematic illustration where a Faraday cell used in a device for sensing glucose in a birefringent medium is shown in PRIOR ART FIG. 1 (which is a schematic illustration of one embodiment shown in the Cameron et al. U.S. Pat. No. 7,245,952 issued Jul. 17, 2007). While such devices can provide ultra-sensitivity and control with the ability to discern and control sub-millidegree rotations in the electric field of light, such devices have several drawbacks. For instance, the Faraday cells are comprised of bulky custom-wound coils thereon. In use, the overdriving can cause coil damage, and the coils are difficult to replace. Additionally, such devices are difficult to tailor-design for custom specifications. Moreover, modulator and compensator operation is provided by two separate devices that each require an expensive optical crystal that has a desirable Verdet constant. In general, a lower Verdet constant require a larger magnetic field. A material with a high Verdet constant is one that has a relatively large amount of polarization rotation under the application of a given magnetic field.

In the past, Faraday-based optical modulation and compensation were performed separately. These Faraday modulators and these Faraday compensators each incorporated their own optical crystal—necessary in order to produce the needed axial magnetic field component for a given rotational depth by winding custom-fabricated inductive coils and placing each crystal in the center of its own coil. Having a separate Faraday modulator and a Faraday compensator requires multiple optical crystals. Proper alignment of these separate optical crystals is problematic and challenging since any light beam diverges after going through the first crystal. The use of multiple optical crystals also requires matching (e.g., optically compatible) optical crystals in order to achieve optical performance. Thus, even crystals purchased from the same vendor often have slight variations unless they came from the same fabrication batch. These variations, in turn, cause a stress birefringence in the light beam passing through the crystals. Furthermore, it is time-consuming and expensive to obtain sufficiently matched optical crystals.

One previous attempt, described in Gobeli U.S. Pat. No. 6,246,893, to combine both Faraday modulation and Faraday compensation with a single crystal mixed the two electric signals, and then applied the combined electric signal to a single inductive coil. One problem with this approach is that mixing the different types of electrical signals (i.e., AC & DC) can be problematic on the high gain AC amplifier side, as these amplifiers often have an inherent DC offset, or drift, which tends to confound or mask the considerably smaller DC compensation drive term needed to achieve optimal performance. As a result, such devices utilizing such an approach cannot be implemented for accurate sensing of certain analytes having a small optical rotation, such as glucose.

To date, there are still many obstacles to the development of a commercially viable and manufacturable product suitable for optical polarimetric glucose detection. Thus, there is a need in the art for improved and more cost-efficient systems for polarimetric and other optical sensing applications.

SUMMARY OF THE INVENTION

Provided herein is an integrated Faraday modulator and compensator system having an AC magnetic field source in a first position in proximity to the optical material, where the AC magnetic field source is configured to generate a first magnetic field; and a DC magnetic field source in a second position in proximity to an optical material, where the DC magnetic field source is configured to generate a second magnetic field. The first position and the second position are configured to cause the first magnetic field and the second magnetic field to be superimposed on the optical material.

In certain embodiments, the optical material comprises a single optical crystal. In certain embodiments, superposition of the first and second magnetic fields within the optical material causes rotational modulation and compensation of a light beam passing through the optical material. In certain embodiments, the optical material is aligned on a first axis, the at least one AC magnetic field source is aligned on a second axis, the at least one DC magnetic field source is aligned on a third axis, where the first, second, and third axes are in a parallel and spaced-apart alignment.

In certain embodiments, one or more spaces are defined between the optical material and the AC magnetic field source or the DC magnetic field source. In certain embodiments, orientation of at least one of the first magnetic field and the second magnetic field is adjustable with respect to the each other and to the optical material. In certain embodiments, each of the AC and DC magnetic field sources is comprised of an inductive coil circumferentially surrounding a ferromagnetic core, and the magnitude of the first magnetic field and the second magnetic field is dependent on the distance from each AC magnetic field source and DC magnetic field source as well as the magnitude of a current driving each inductive coil, while the direction of each magnetic field is perpendicular to a plane formed by the intersection of the current and separation vectors using Equation 4:

$$B(r) = \frac{\mu_0}{4\pi} \oint \frac{I \times R}{R^3} dr_0;$$

where bolded terms represent vector quantities, B(r) is the magnetic field at any point in space a distance r from the origin, $\mu_0$ is the permeability of free space ($4\pi \times 10^{-7}$ N/A$^2$), I is the current, R is the vector directed from the source point to r, and $dr_0$ is an element of length along the current path.

In certain embodiments, the first magnetic field is generated by an AC current from a first power source, and the second magnetic field is generated by a DC current from a second power source. In certain embodiments, each of the AC and DC magnetic field sources is comprised of an inductive coil circumferentially surrounding a ferromagnetic core, where each the ferromagnetic cores defines an axis that is parallel to, and annularly spaced at about 90° intervals around, an axis defined by the optical material.

In certain embodiments, the integrated Faraday modulator and compensator (IFMC) system has a modulation depth of about 1° and a maximum compensation depth of about 0.0632°. In certain embodiments, the AC magnetic field source comprises a high-powered resonant circuit having one or more inductive coils and a magnetic core. In certain embodiments, the AC magnetic field source comprises a ferromagnetic core and an electrically driven coil. In certain embodiments, different size, shape, and/or inductances of the coil provides a desire operational range of rotations based on the maximum voltage supplied to the AC magnetic field source.

In certain embodiments, the AC magnetic field source comprises a vibrationally mounted permanent magnet. In certain embodiments, the AC magnetic field source comprises at least one 100 mH inductor. In certain embodiments, the AC magnetic field source is comprised of a low-powered resonant circuit having one or more inductive coils and a magnetic core. In certain embodiments, the DC magnetic field source comprises a ferromagnetic core and an electrically driven coil. In certain embodiments, different size, shape, and/or inductances of the coil provides a desire operational range of rotations based on the maximum voltage supplied to the DC magnetic field source.

In certain embodiments, two or more AC magnetic field sources are connected in series such that current flows in the same direction around each coil, producing a collectively maximized axial component of the magnetic field along the optical material, and achieving an effective Faraday modulation to light passing through the optical material.

In certain embodiments, the optical material comprises a terbium-doped glass (TDG) material; a terbium gallium garnet (TGG) material; or, an yttrium iron garnet (YIG) material. In certain embodiments, the optical material has a length-to-diameter aspect ratio of about 2.5. In certain embodiments, the optical material has a length of about 13.5 mm and a diameter of about 5.4 mm.

Further provided herein is a method of conducting integrated Faraday modulation and Faraday compensation, the method comprising generating a first magnetic field from an AC current, generating a second magnetic field from a DC current, and superimposing the first magnetic field and the second magnetic field onto a single optical material.

Further provided herein is a method of measuring changes in a state of polarization of a beam of light, the method comprising generating a first magnetic field from an AC current, generating a second magnetic field from a DC current, and superimposing the first magnetic field and the second magnetic field onto a single optical material.

Further provided herein is a method of measuring changes in a state of polarization in a sample, the method comprising (a) passing polarized light through a sample or reflected from a surface of the sample such that the state of polarization of the light is changed; (b) allowing the changed polarized light of step a) to pass through an optical material having a desired Verdet constant; (c) providing separate AC and DC magnetic field sources to the optical material; the AC magnetic source producing a first magnetic field for fast polarization modulation; and, the DC magnetic source producing a second magnetic field for polarization feedback compensation; (d) superimposing the separate first and second magnetic fields within the optical material as the polarized light of step b) passes through the optical material of step c); (e) passing the polarized light of step d) through an analyzer; (f) allowing the light of step e) to impinge onto a detector; (g) providing a feedback signal to at least one DC magnetic field source; (h) measuring changes in a state of polarization in the sample; and, optionally (i) adjusting at least one DC magnetic field source based on the feedback signal of step g).

In certain embodiments, changes in the state of polarization are calibrated, based on the feedback signal of step g), to one or more of: concentration of an analyte in the sample, layer thickness of the sample, surface characteristics of the sample, and material comprising the analyte and/or sample. In certain embodiments, step h) includes varying ranges of modulation depths and/or varying ranges of compensation depths of one or more of the magnetic fields. In certain embodiments, the method further includes step j) controlling modulation and compensation depth by varying one or more of parameters selected from: coil permeability, conductivity, wire radius, or number of turns, in the AC and/or DC magnetic field sources; location of the AC and/or DC magnetic field sources with respect to each other and/or to the optical material; orientation of the AC and/or DC magnetic field sources with respect to each other and/or to the optical material; and, current drive within the AC and/or DC magnetic field sources.

In certain embodiments, the sample is an optically active material. In certain embodiments, the optically active material comprises glucose. In certain embodiments, the glucose is present in aqueous humor of an eye, and the method comprises detection of glucose concentrations through the aqueous humor of the eye.

In certain embodiments, the sample comprises a material having surface variations. In certain embodiments, the material having surface variations comprises a thin film material.

In certain embodiments, a component apparatus is adjustable to allow for an operational range for modulation between 0° and 2°. In certain embodiments, a component apparatus is adjustable to allow for an operational range for compensation between 0° and 0.5° with sub-millidegree rotational sensitivity. In certain embodiments, the method comprises achieving a modulation depth of about 1° and a maximum compensation depth of about 0.0632°.

In certain embodiments, an AC power supply to the AC magnetic field source sustains a desired modulation depth to the magnetic fields being supplied to the optical material, and a DC power supply to the DC magnetic field source supplies a sub-millidegree rotational sensitivity to the magnetic fields being supplied to the optical material.

Further provided herein is an integrated Faraday modulator and compensator (IFMC) component apparatus comprising: a modular housing defining a plurality of cavities configured position, with respect to each other: (i) an optical material; (ii) at least one AC magnetic field source disposed in a first position in proximity to the optical material, the AC magnetic field source being configured to generate a first magnetic field; and, (iii) at least one DC magnetic field source disposed in a second position in proximity to the optical material, the DC magnetic field source being configured to generate a second magnetic field; the apparatus further comprising a first power source disposed outside the modular housing and configured to supply an AC current to the AC magnetic field source, and a second power source disposed outside the modular housing and configured to supply a DC current to the DC magnetic field source.

In certain embodiments, the apparatus further includes a polarizer disposed outside the modular housing and configured to supply polarized light through the optical material. In certain embodiments, the apparatus further includes an analyzer disposed outside the modular housing and configured to receive modulated and compensate light from the IFMC system. In certain embodiments, the apparatus further includes a detector disposed outside the modular housing and configured to receive modulated and compensate light from the analyzer. In certain embodiments, the apparatus further includes a feedback signaling system disposed outside the modular housing and configured to receive modulated and compensate light from the detector and configured to provide a feedback signal to at least one DC magnetic field source.

Various objects and advantages of this invention will become apparent to those skilled in the art from the following detailed description of the preferred embodiment, when read in light of the accompanying drawings.

BRIEF DESCRIPTION OF THE DRAWING

PRIOR ART FIG. 1: Schematic illustration of a glucose sensing polarimeter utilizing a separate Faraday modulator and a separate Faraday compensator.

FIG. 19A is a calibration graph of hypoglycemic glucose detection. FIG. 19B is a calibration graph of hyperglycemic glucose detection. FIG. 19C is a validation graph of hypoglycemic glucose detection. FIG. 19D is a validation graph of hyperglycemic glucose detection.

DETAILED DESCRIPTION OF THE INVENTION

Figure 2A:
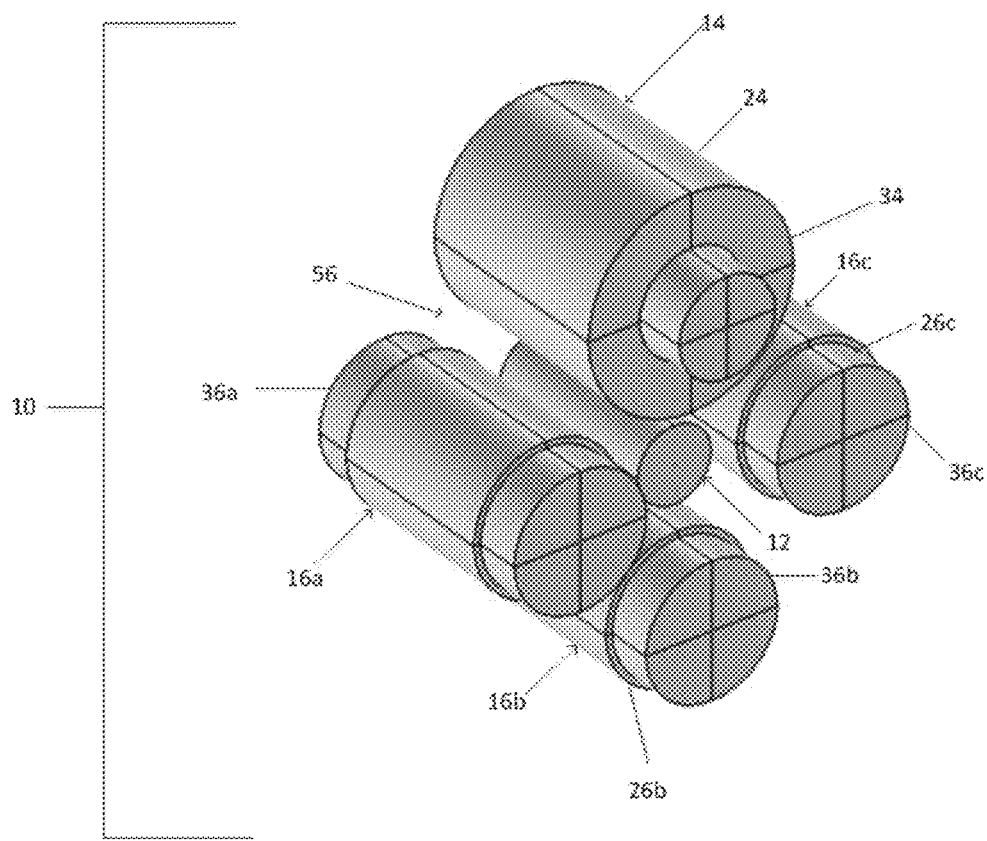
FIG. 2A: Exploded perspective schematic illustration of one embodiment of an integrated Faraday modulator/compensator (IFMC) system.

Throughout this disclosure, various publications, patents and published patent specifications are referenced by an identifying citation. The disclosures of these publications, patents and published patent specifications are hereby incorporated by reference into the present disclosure in their entirety to more fully describe the state of the art to which this invention pertains.

General Description

Optical polarimetry is the measurement of the polarization state of transverse electromagnetic waves (TEM). More specifically, a polarimeter is a device capable of measuring rotation in the state of linear polarization when a transverse electromagnetic wave passes through an optically active material, such as glucose. A material is optically active if the electric field of a linear plane wave rotates around an axis parallel to the direction of travel through the material. These types of materials are classified based on the direction of rotation in the electric field. If a plane wave rotates in a clockwise (positive) direction when facing the source of light, the material is dextrorotatory (d-rotatory). If a wave rotates in a counterclockwise (negative) direction, it is levorotatory (l-rotatory). Optically active materials possess a separate refractive index that affects right ($n_R$) and left ($n_L$) circularly polarized light, a material property known as circular birefringence. Given that the linear polarization is the superposition of two opposing circular components of equal magnitude, the components become out of phase when travelling through an optically active material, resulting in a rotated plane wave. The amount of rotation ($\alpha$) can be quantified based on the indices of refraction, material path length (L), and vacuum wavelength ($\lambda_0$), as shown in Equation 1:

$$\alpha = \frac{180° L}{\lambda_0}(n_L - n_R) \qquad \text{Equation 1}$$

The concept of optical activity holds true for glucose and other chiral molecules when dissolved in solution, based on their overall concentration. Chiral molecules have multiple enantiomers, which are identical compounds except in how they react with other chiral molecules and in how they rotate linearly polarized light. Complex biological molecules, such as glucose, typically occur in nature as one enantiomer, meaning that a net rotation in polarization can be observed in samples containing these compounds. The relationship between rotation, sample path length, and concentration (C) is given as a temperature-(T), wavelength-($\lambda$), and pH-dependent constant known as specific rotation, $[\alpha]_{\lambda,pH}^T$, as shown in Equation 2:

$$[\alpha]_{\lambda,pH}^T = \frac{\alpha}{LC} \qquad \text{Equation 2}$$

Given the specific rotation of D-glucose (63.2°/(dm*g/mL) at 543.5 nm), a physiological change of 10 mg/dL in concentration results in a rotational shift of 0.632 millidegrees in a linearly polarized beam of light when passed through a 1 cm sample. Therefore, a noninvasive polarimetric detection system for glucose detection should be able to achieve sub-millidegree measurement sensitivity.

Although signal modulation allows for significant noise rejection, the detection source of a polarimeter should still be capable of measuring sub-millidegree rotations. Therefore, a null-point, closed-loop signal feedback mechanism that can controllably compensate for signal rotation caused by glucose can be utilized. When digitally controlled, the feedback mechanism can detect glucose concentrations in real time. In order to control rotational modulation and compensation in a real-time, closed-loop system, a phenomenon known as Faraday rotation can be utilized. This method of rotation is similar to that which occurs in an optically active medium. However, the oscillating electric field component of the propagating light causes elastically bound electrons within an optical material to vibrate in a circular orbit. The generation of this current in combination with the axial component of an external magnetic field produces a force on the electrons. This force, along with the elastic restoring force of the electrons, creates two separate dipole moments, leading to two separate indices of refraction ($n_R$ and $n_L$), and ultimately causing circular birefringence. The relationship between rotation ($\alpha$), path length (L), and the magnetic field strength in the direction of travel (B) is held by a temperature- and wavelength-dependent proportionality constant known as the Verdet constant (V) as shown in Equation 3:

$$\alpha = VBL \qquad \text{Equation 3}$$

Materials which typically experience this phenomenon, such as terbium gallium garnet (TGG) and terbium-doped glass (TDG), can be very expensive and difficult to produce such that stress- and temperature-induced birefringence do not play a role in rotational interference.

Faraday rotation is most useful in polarimetry for its ability to controllably modulate and compensate polarized light. The precise control required for sub-millidegree rotation sensitivity is achieved through voltage-driven inductive coils based on the relationship between a moving charge and magnetic field as shown in the Biot-Savart Law:

$$B(r) = \frac{\mu_0}{4\pi} \oint \frac{I \times R}{R^3} dr_0 \qquad \text{Equation 4}$$

Bolded terms in Equation 4 represent vector quantities, B(r) is the magnetic field at any point in space a distance r from the origin, $\lambda_0$ is the permeability of free space ($4\pi \times 10^{-7}$ $N/A^2$), I is the current, R is the vector directed from the source point to r, and $dr_0$ is an element of length along the current path. As seen in Equation 4, the magnitude of the magnetic field is dependent on the distance from the source as well as the magnitude of the driving current, while the direction of the field is perpendicular to the plane formed by the intersection of the current and the separation vectors.

Figure 5A:
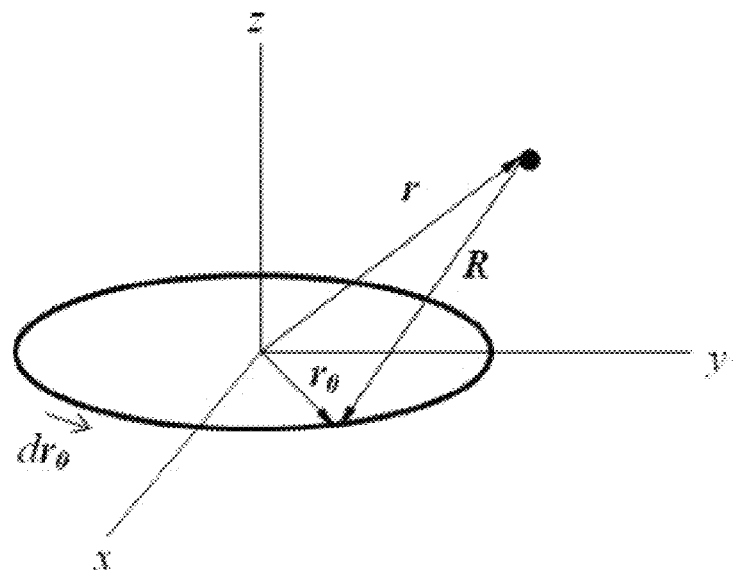
FIG. 5A: Schematic illustration of a single loop of current as applied to the Biot-Savart Law.

It is to be understood that the concept of Faraday rotation is only dependent on the field component that is parallel to the axis of travel of the light source and inductive coils are typically used to generate this component. The representation of a single loop of current from an inductor as applied to the Biot-Savart Law can be seen in FIG. 5A. Based on this geometry, it can be seen that $r_0 = r_0 \cos(\theta)\hat{x} + r_0 \sin(\theta)\hat{y} + z_0\hat{z}$, $r = x\hat{x} + y\hat{y} + z\hat{z}$, $R = r - r_0 = [x - r_0 \cos(\theta)]\hat{x} + [y - r_0 \sin(\theta)]\hat{y} + [z - z_0]\hat{z}$, and $dr_0 = [-r_0 \sin(\theta)\hat{x} + r_0 \cos(\theta)\hat{y}]d\theta$ since $r_0$ is constant around the loop. By holding the current constant, as is the case in the Faraday compensator, it can be moved outside of the integral and the cross product of $dr_0$ and R can be solved. The vector quantity Q was arbitrarily assigned as the solution to this cross product as given by:

$$Q_x = [zr_0 \cos(\theta) - z_0 r_0 \cos(\theta)]d\theta\hat{x} \qquad \text{Equation 5}$$

$$Q_y = [zr_0 \sin(\theta) - z_0 r_0 \sin(\theta)]d\theta\hat{y} \qquad \text{Equation 6}$$

and, $$Q_z = [r_0^2 - yr_0 \sin(\theta) - xr_0 \cos(\theta)]d\theta\hat{z} \qquad \text{Equation 7}$$

By letting $\alpha = x^2 + y^2 + z^2 + z_0^2 + r_0^2 - 2zz_0$, the magnitude of the separation vector R can be calculated to be $$R = \sqrt{\alpha - 2xr_0\cos(\theta) - 2yr_0\sin(\theta)} \qquad \text{Equation 8}$$

Finally, Equations 5 through 8 can be substituted into Equation 4 and the component representation of the magnetic field from a single, uniform loop of current at any point in space can be given as $$B_x(x, y, z) = \frac{\mu_0 I}{4\pi} \oint_0^{2\pi} \frac{[zr_0\cos(\theta) - z_0 r_0\cos(\theta)]}{[\alpha - 2xr_0\cos(\theta) - 2yr_0\sin(\theta)]^{3/2}} d\theta \qquad \text{Equation 9}$$

$$B_y(x, y, z) = \frac{\mu_0 I}{4\pi} \oint_0^{2\pi} \frac{[zr_0\sin(\theta) - z_0 r_0\sin(\theta)]}{[\alpha - 2xr_0\cos(\theta) - 2yr_0\sin(\theta)]^{3/2}} d\theta \qquad \text{Equation 10}$$

and, $$B_z(x, y, z) = \frac{\mu_0 I}{4\pi} \oint_0^{2\pi} \frac{[r_0^2 - yr_0\sin(\theta) - xr_0\cos(\theta)]}{[\alpha - 2xr_0\cos(\theta) - 2yr_0\sin(\theta)]^{3/2}} d\theta \qquad \text{Equation 11}$$

Based on Equations 9, 10, and 11, it can be seen that solving for the magnetic field at a single point in space due to a loop of current will require complex numerical integration. Given that a coil inductor can be viewed as a series of current loops when in steady state, superposition can be used to evaluate the total field strength at various points in space. However, these calculations get progressively more complex when different materials, shapes, and orientations are evaluated with multiple inductors at several points in space. Also, the model no longer holds true in an AC driven coil, such as that required for Faraday modulation. As such, described further herein is a finite element model (FEM) which is a computational method capable of solving thousands of ordinary differential equations (ODEs), partial differential equations (PDEs), and integral equations simultaneously over complicated domains by solving a matrix of nodes applied with initial conditions based on the materials and physics used. The FEM was designed for accurate and efficient field calculations in both compensator and modulator coils.

In use, a Faraday modulator modulates the electric field vector by imposing a certain frequency. Such modulation, in turn, creates a large AC signal. In use, a Faraday compensator negates (e.g., compensates for) the optical rotation of the optically active sensor. Such compensation, in turn, creates a small DC signal.

The operation of a Faraday-based, closed-loop, null-point feedback polarimeter can be modeled mathematically using Jones vectors and matrices which are used to represent the electric field of polarized light and how it interacts with various optical components. A Jones vector is a component representation of the electric field of a polarized wave. Different optical components are represented as Jones matrices which describe the behavior of polarized light through a specific component. By multiplying the vector representation of the polarized electric field by various Jones matrices, the behavior of an optical system such as a polarimeter can be predicted. This technique is especially useful to represent the light intensity that is measured by a photodetector in Faraday-based optical polarimetry. The Jones model used to represent the detected signal intensity in such a system is shown in Equation 12:

$$E^2 = \left(\phi^2 + \frac{\theta_m^2}{2}\right) + 2\phi\theta_m\sin(\omega_m t) - \frac{\theta_m^2}{2}\cos(2\omega_m t) \qquad \text{Equation 12}$$

where $\phi$ is the difference in rotation between the optically active sample and that of the Faraday compensator, $\theta_m$ is the modulation depth, $\omega_m$ is the modulation frequency, and t is time. The model has three components: a DC offset, a modulated component, and a $2\omega_f$ component. The $2\omega_f$ component is present because photodetectors are only sensitive to light intensity, which is always a positive value. Therefore, when the rotational modulation is centered on the null plane of the analyzer, it appears as though the detected signal has a frequency that is twice the driving frequency due to rotational symmetry. However, when an optically active sample is introduced, the rotational modulation is no longer centered on the null plane, so a single frequency component exists as well. When this occurs, the lock-in amplifier detects the single frequency component and produces an output based on the non-orthogonal relationship to the reference sine wave. The principle of the null-point feedback system is to continuously apply a DC voltage to the compensator coil that is proportional to the magnetic field and, in turn, the amount of rotation caused by the optically active sample in order to force $\phi$ to zero. This is done by continuously measuring the lock-in output and compensating for rotations in polarization by a digital proportional-integral-derivative (PID) controller. When the signal is completely nulled, only the $2\omega_f$ component is present, the lock-in output is zero, and the PID output corresponds to the concentration of glucose within a fixed-length sample. The compensator voltage can then be correlated to the glucose concentration through least-squares linear regression, and the model can be used to predict unknown concentrations.

Electro-optic modulators and compensators (EOMs) are optical devices capable of imposing or affecting the phase, frequency, amplitude, or polarization of light. Various forms of EOMs exist, and they are not limited to Faraday cells. Some other exemplary types of EOMs include liquid crystals, Pockels cells, Kerr cells, and photoelastic modulators.

In a Faraday cell, the core of the device is an optical rod doped with paramagnetic ions. The Faraday rotation of the electric field ($\beta$) is proportional to the product of the Verdet (V) constant of the optical crystal and the magnetic field (B) across the length (d) of the crystal, as illustrated in Equation 3:

$$\beta = VBd \qquad \text{Equation 3}$$

Integrated Faraday Modulator/Compensator (IFMC) System

Described herein is an integrated Faraday modulator/compensator (IFMC) system that keeps electric signals separate, and then combine the signals in the magnetic field. In such embodiments, two magnetic fields are produced from two separate electric signals, and are then combined on the optical material; when the magnetic fields of the two electric signals are in the same time and space, they superimpose on top of each other. This eliminates the problem of DC drift from mixing electric signals, and eliminates the need for a second optical crystal, while still maintaining desired performance characteristics.

Figure 2B:
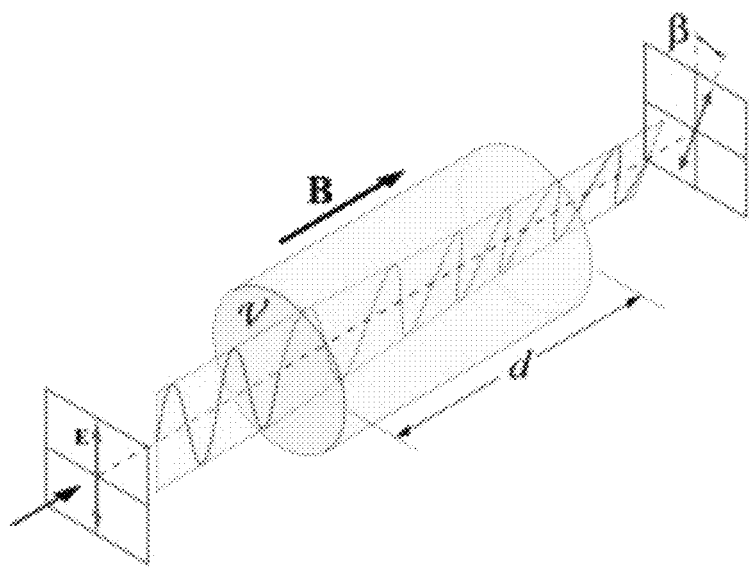
FIG. 2B: Schematic illustration of β=VBD, where a magnetic field correlates to Faraday rotation via Verdet constant.

The IFMC system provides control of Faraday rotation through the magnetic field, which is generated from current travelling around an inductive coil. FIG. 2A shows an exploded perspective schematic illustration of one embodiment of an integrated Faraday modulator/compensator (IFMC) system 10, while FIG. 2B provides a schematic illustration of $\beta=VBD$, where a magnetic field correlates to Faraday rotation via the Verdet constant.

In the embodiment shown in FIG. 2A, the IFMC system 10 includes an optical component 12, at least one compensator 14 (e.g., source of a DC magnetic field 14), and at least one modulator 16 (e.g., source of an AC magnetic field 16). The compensator 14 illustrated in FIG. 2 includes coils 24 wound around a ferromagnetic core 34. In the embodiment shown in FIG. 2, a plurality of modulator components 16a, 16b, 16c are shown. Each modulator 16 illustrated in FIG. 2 includes coils 26a, 26b, 26c, respectively, wound around ferromagnetic cores 36a, 36b, 36c, respectively.

It is to be understood that, while one geometrical configuration of the IFMC system 10 is shown in FIG. 2A, many other configurations are possible. For example, in certain embodiments, the IFMC system 10 can have more than one compensator component 14 and/or one or more modulator components 16.

Certain embodiments of the IFMC system include gaps 56 between the compensator component 14 and the optical crystal, and/or between the modulator components 16 and the optical crystal 12. The gaps 56 allow for air flow channels to be created, reducing the amount of heating on the crystal 12. Furthermore, in certain embodiments, the IFMC system 10 requires less power since there can be fewer windings in the compensator coil 24 and/or the modulator coils 26 than in previous devices, thus further reducing the heating on the crystal 12.

In general, the IFMC system has two or more inductive coils that are placed within close proximity to the optical material, one for modulation and one for compensation. The location and orientation of the inductive coils with respect to the optical material within the housing or component apparatus can be controlled by fixture inserts and spacers. Coil type selection, location, orientation, and drive characteristics are variables that can be used to control modulation and compensation depth, so as to customize the IFMC system for specific applications. Mathematical or computational models can be used for predicting rotational characteristics based on component apparatus parameters.

In certain embodiments, the DC magnetic field source 14 is composed of a separate inductive coil for highly sensitive rotational control. Rotational modulation and compensation occurs within the optical component by the superposition of separate magnetic fields within the optical material. In certain embodiments, the AC magnetic field source 16 is composed of a high-powered resonant circuit having of one or more inductive components within close proximity to the optical material 12, or a vibrationally mounted permanent magnet within close proximity to the optical material 12.

The IFMC system 10 integrates the functionality of both polarization modulation and compensation in a single-crystal system while maintaining performance standards. Separate Faraday components are not needed, and a single optical material can be used for both modulation and compensation based on the superposition of magnetic fields from separate inductive components. In the embodiment shown, ferrite-core inductors can be placed within proximity of the optical material in order to provide the necessary field strength along a longitudinally extending axis of the optical material. In certain embodiments, the IFMC system does not require specially designed custom inductive coils because it is capable of utilizing standard commercially-available inductive coils to achieve required performance. In certain embodiments, the IFMC system has a modular design which can be easily adapted for specific applications requiring different performance standards.

Figure 3:
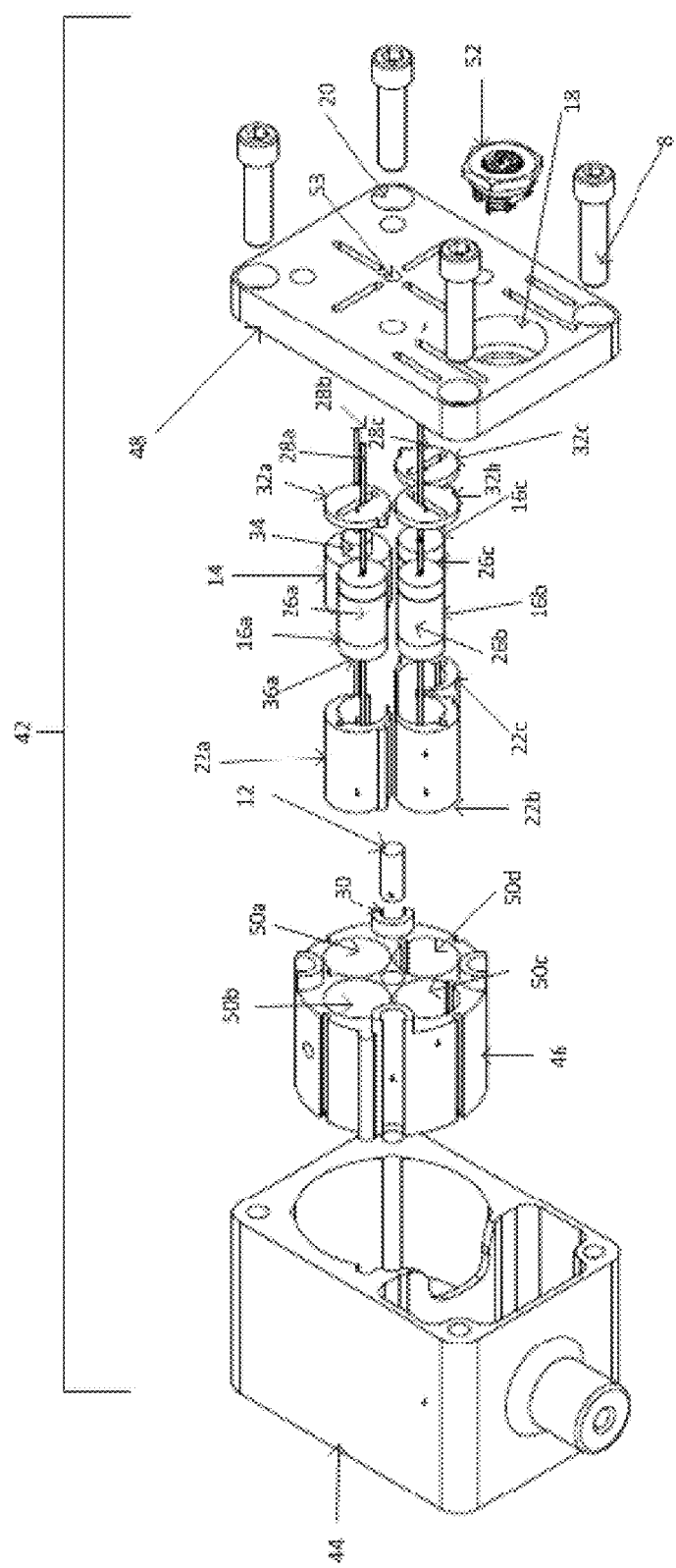
FIG. 3: Exploded perspective schematic illustration of an IFMC system integrated in to a device for measuring of measuring changes in a state of polarization in a sample.

Referring now in particular to FIG. 3, one embodiment of the IFMC system can be included in a modular unit 42 having an outer housing 44 and an inner housing 46, where the outer housing 44 is fastened to a cage mount 48 via one or more mounting bolts 8. The inner housing 46 has one or more fixture slots 50a, 50b, 50c, 50d designed to house the optical crystal 12, modulator components 16a, 16b, 16c, and compensator component 14. The optical crystal 12 is held in place with a clamp 30. The modulator components 16a, 16b, 16c are composed of inductive coils 26a, 26b, 26c wrapped around ferromagnetic cores 36a, 36b, 36c, each contained within a body shell 22a, 22b, 22c and a cap 32a, 32b, 32c. The compensator component 14 is composed of an inductive coil 24 wrapped around a ferromagnetic core 34. The compensator 14 is held in place with an insert rod 28a, and each of the modulators 16a, 16b, 16c is held in place with an insert rod 28b, 28c, 28d.

As shown in FIG. 3, the modular unit 42 utilizes multiple inductors: at least one modulator coil 26 and a compensator coil 24. Each inductor coil 24, 26 can be driven with a different signal. Each inductor coil 24, 26 generates a respective magnetic field. The two magnetic fields are then combined. The inductive coils 24, 26 can be placed in parallel or in series; many designs are possible. The specific coils to use and the exact design of the coils depends on the application; the geometry and design of the coils can be tailored specifically and optimized for the desired application using a FEM as described herein. In certain embodiments, the ends of the coils are connected to separate power supplies.

In certain embodiments, the optical crystal 12 is in a position where the compensator coil 24 and the modulator coils 26a, 26b, 26c are arranged annularly around, and in close proximity to, the optical crystal 12, as shown in FIG. 3. However, in certain embodiments, the optical crystal 12 need not be oriented in the center of the housing 4 or the coils 14, 16, and the compensator 14 and/or modulators 16 need not be in an annular arrangement. In certain embodiments, the optical crystal 12 is in a spaced-apart relationship to the compensator 14 and the modulators 16 such that one or more gaps 56, or air flow channels, exist between the optical crystal 12 and the compensator 14 and the modulators 16, as seen in FIG. 2A.

In the embodiment shown in FIG. 3, the cage mount 48 has an optical window 53 configured to allow electromagnetic radiation from a light source, such as a laser, to pass through the modular unit 42. An associated plug 52 for the electrical connections to the drive electronics is inserted into the plug mount 18. The cage mount 48 and the outer housing 44 can also have multiple connection ports 20 that are configured to physically integrate the modular unit 42 into a polarimetric or other optical sensing system (for example, see FIG. 20, discussed below). It is to be understood that many alternative designs for a modular IFMC system 10 are possible, and are within the contemplated scope of the disclosure herein.

The outer housing 44 for the IFMC system 10 can be formed to suit a desired end-use application. For example, in one embodiment, the housing 44 can be manufactured through a three-dimensional printing process, using for example SolidWorks® structural models, or any other similar techniques. The ability to custom-tailor a housing 44 allows for custom IFMC systems to be designed to meet particular specifications for a given end-use application.

The optical crystal 12 in the IFMC system 10 can be a suitable optical crystal 12 that exhibits the Verdet property. Suitable optical crystals 12 include, but are not limited to, terbium gallium garnet (TGG) crystals, terbium-doped glass (TDG) crystals, and yttrium iron garnet crystals. In certain embodiments, the IFMC system 10 utilizes a single TDG crystal having a generally rod-shape, and inductive coils that are capable of replacing the custom designed components used in traditional Faraday-based systems. Suitable inductive coils 24, 26 include, but are not limited to, ferrite core inductors. The utilization of ferromagnetic cores 34, 36 such as ferrite cores, can result in reduced power consumption compared to other designs. Combined, the use of a single optical crystal and ferrite core inductors significantly minimizes size and cost by eliminating the need for custom-designed coils and multiple optical components.

The IFMC system 10 also overcomes the problem plaguing the art of coil heating, which can affect crystal properties by causing thermal instability—where an inductive coil is wrapped around the crystal, such that when the coil heats up, the crystal is also heated.

Finite Element Model (FEM)

The single-crystal modular design of the IFMC system 10 can use different types of ferromagnetic core inductors. In another aspect, there is provided herein a finite element model (FEM) system which allows for further customization of the IFMC system 10.

Figure 4A:
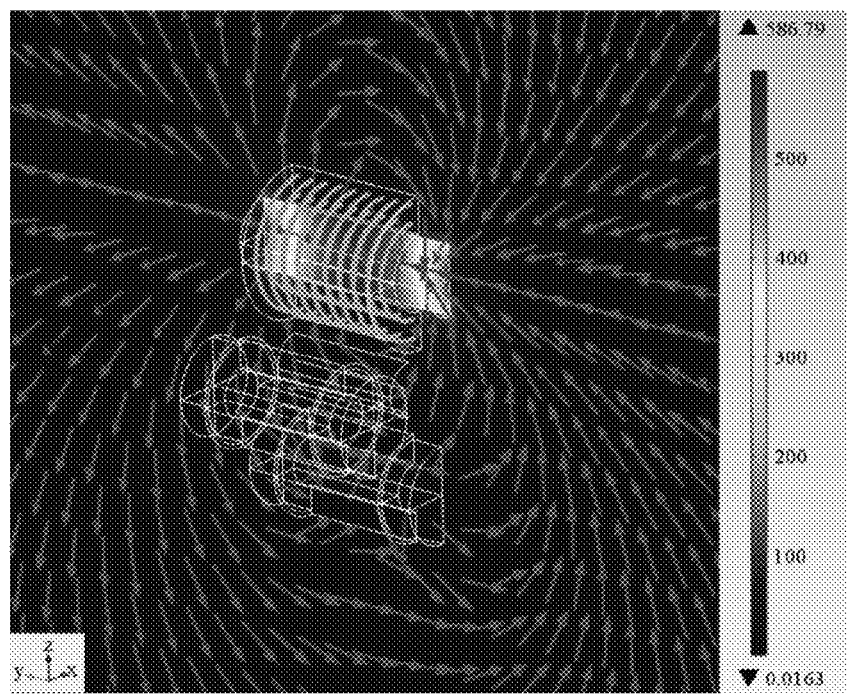
FIGS. 4A-4B: Three-dimensional color map plot of magnetic field (G) of an IFMC system in compensation (FIG. 4A), and modulation (FIG. 4B) after a finite element model (FEM) analysis. The green curved lines represent the direction of current and the red arrows represent the field direction.
Figure 4B:
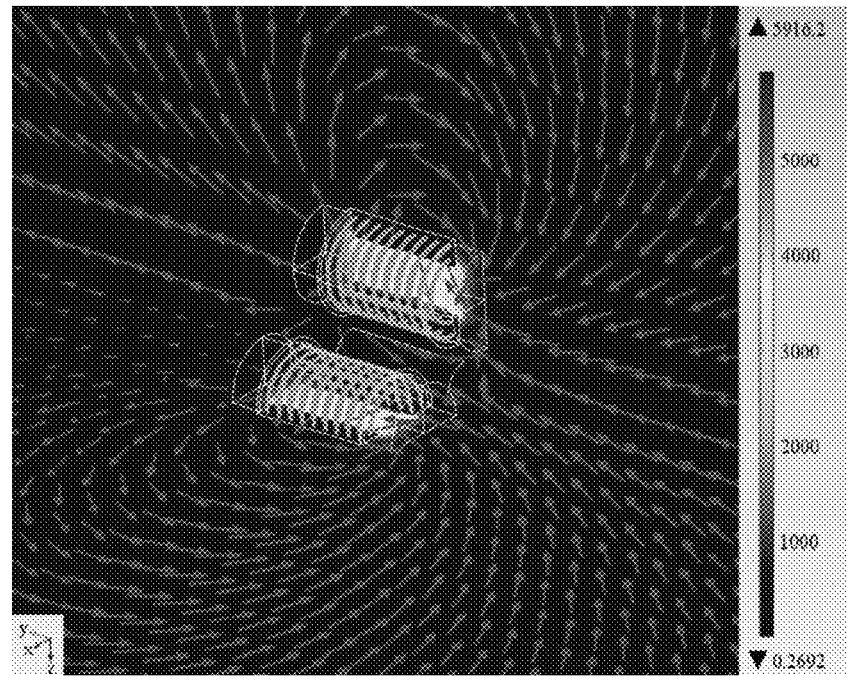

For example, without a model, the inductor identification, placement, and interaction can be difficult to characterize in order to achieve a required performance. This is generally because the addition of non-uniform shapes, various materials, and non-symmetric orientations make predictive calculations extremely complex. Thus, provided herein is a non-limiting example of optimization for specific design specifications using a robust three-dimensional (3D) finite-element-model (FEM) system. The FEM uses magnetic fields, such as those illustrated in FIGS. 4A-4B. The FEM can completely simulate a particular design of an IFMC system 10, thus enabling the IFMC system to be custom-designed for specific user specifications.

The FEM allows for off-the-shelf components to be optimized to achieve certain operational parameters. For example, a user could specify a predefined modulation depth and compensation range. The 3D model can then be used to identify the required, commercially available inductive components and the necessary layout to meet the required specifications. Any issues with the generation of the magnetic/electric field can be verified through the 3D visualization and can be addressed before the actual device is assembled.

Examples of Applications

The systems, devices and methods disclosed herein are useful for polarimetric and other optical sensing applications, and involve measuring changes in the state of polarization of light by the superposition of magnetic fields for combined Faraday-based modulation and compensation. In certain embodiments, polarized light is passed through a sample or reflected from a surface such that the state of polarization changes. The light is then allowed to pass through a component containing an optical material, such as a terbium-containing compound, which is within close proximity to separate AC and DC magnetic field sources. The AC magnetic field source produces a high-powered AC magnetic field for fast polarization modulation, while the DC magnetic field source produces a lower-powered DC magnetic field for polarization feedback compensation. The separate magnetic fields are superimposed in time and space within the optical material through which the light also passes. The light then passes through an analyzer prior to impinging onto a detector. In certain embodiments, feedback from the system utilizes a highly sensitive, lower-powered DC magnetic field source to nullify the polarization offset corresponding to the sample of interest.

The IFMC system can be used for detecting changes to the state of polarization in the light signal due to optically active materials or surface variations. A non-limiting example of such an application involves the noninvasive detection of glucose concentrations through the aqueous humor of the eye. Changes in the state of polarization can be calibrated to concentration, layer thickness, surface characteristics, or material percentage based on the feedback signal. The separation of AC and DC magnetic field sources allows for highly sensitive rotational measurements, easy customization to specific applications, the use of a single optical material component, and a wide range of modulation depths capable of being combined with a wide range of compensation depths.

In certain embodiments, the design parameters of the IFMC system allow for an operational range for compensation between 0° and 0.5° with sub-millidegree rotational sensitivity. The separation of the magnetic field sources allows for highly sensitive control of separate drive electronics for modulation and compensation; that is, high-powered drive electronics can sustain the required modulation depth while a low-powered DC supply can provide sub-millidegree rotational sensitivity without interference from mixed signals. The superposition of the separate magnetic fields provides stabile modulation and highly-sensitive compensation in a single optical component device for rotational measurements.

In certain embodiments, the IFMC system can achieve modulation depths above 1°, and when operating in a compensated closed-loop glucose-sensing polarimetry configuration, can achieve glucose prediction errors of 1.8 mg/dL and 5.4 mg/dL under hypoglycemic and hyperglycemic conditions, respectively.

The IFMC system can be implemented into multispectral systems for further component consolidation in multi-analyte or birefringent conditions. Drift in such systems comprising an IFMC system may be minimized by rigidly coupling the optical components together and eliminating excess vibration in a compact, hand-held device. The IFMC system is particularly versatile when miniaturized so as to fit into a hand-held instrument. In certain embodiments, the IFMC system has no moving parts, and therefore is free of mechanically produced noise problems.

In certain embodiments, the IFMC system and methods described herein provide optimized application-specific performance using lower-cost fabrication components with a modular design approach. Sub-millidegree control for linear polarization applications is possible with an IFMC system.

Though various examples pertaining to glucose sensing are described herein, it is to be understood that the IFMC system is not limited to use in glucose-monitoring applications. Rather, the IFMC system is also suitable for use in a wide variety of applications and instruments, including any type of device that incorporates modulators. By way of non-limiting examples, the IFMC system is also useful in devices, instruments, or systems for Fourier transform infrared (FTIR) spectroscopy, optical coherence tomography, and optically-active Raman spectroscopy.

The IFMC system can also be utilized in devices for sensing any optically active analyte including, but not limited to, glucose, lactic acid, albumins, and proteins. The IFMC system is particularly useful for thin-film ellipsometry and in vivo and multi-analyte noninvasive sensing.

Examples of FEM

Optimization for specific design specifications can be provided through FEM. Use of such FEM allows for the IFMC system to be tailor-designed for custom applications, or to minimize power consumption Minimizing power consumption, while still maintaining operational specifications, is especially important for hand-held devices so that they can be powered through rechargeable battery subsystems.

Another benefit of using a FEM is that various spatially dependent variables can be solved within a complex geometry with varying material properties through discrete methods. Through the FEM, the volume or surface of interest is divided into an array of discrete elements of finite size and shape. Each element is assigned a specific set of material properties based on the physics that are being solved, such as electrical conductivity, magnetic permeability, and electrical permittivity in the case of electromagnetic fields. The array of elements together is known as the mesh, which is used to collectively define the overall system.

The size of individual elements throughout the mesh may vary depending on the intricacies of the model in order for the analysis to converge to a representative result. The intersections of elements create analysis points, or nodes, which provide points in space that can numerically represent a solution. Various systems of equations can then be assigned to the model, which are solved using discrete numerical and computational methods based on a set of initial boundary conditions applied to the model and the interactions between individual elements. Such models allow for multiple ordinary and partial differential, as well as integral, equations to be solved simultaneously, depending on the approximations within each finite element. The results can be compiled as a fully integrated model in order to represent collective interactions at various regions of interest. The mathematical theory involved is based on the Galerkin method, which can be used to convert continuous problems into discrete approximations.

There are several software applications suitable for solving FEMs with a heavy focus on structural mechanics. COMSOL® Multiphysics is one such package, which can solve models implementing several complementary physics such as structural mechanics, thermodynamics, fluid flow, chemical reactions, and electromagnetism based on independent or dependent interactions. The AC/DC Module within COMSOL® allows for the analysis of magnetic field physics in three-dimensional structures. The magnetic fields interface within this module solves Ampere's Law for the magnetic vector potential based on the following equations:

$$J_e = (j\omega\sigma - \omega^2 \epsilon_0 \epsilon_r) A + \nabla \times (\mu_0^{-1} \mu_r^{-2} B) - \sigma v \times B \qquad \text{Equation 14}$$

$$B = \nabla \times A \qquad \text{Equation 15}$$

where $J_e$ is the external current density, j is the imaginary unit, $\omega$ is frequency, $\sigma$ is conductivity, $\epsilon_0$ is the vacuum permittivity, $\epsilon_r$ is the relative permittivity, A is the vector potential, $\nabla$ is the del operator, $\mu_0$ is the vacuum permeability, $\mu_r$ is the relative permeability, B is the magnetic field vector, and v is the current velocity vector of the conductor. These equations can be solved in both static and frequency-dependent conditions, providing an ideal system for predicting Faraday rotations in compensation as well as frequency-dependent modulation.

Also provided herein is a method of using such results to optimize a Faraday-based optical polarimeter for a variety of applications. Given that a coil inductor can be viewed as a series of current loops when in steady state, superposition can be used to evaluate the total field strength at various points in space in a multi-turn coil. However, these calculations get progressively more complex when different materials, shapes, and orientations are evaluated with multiple inductors at several points in space. Thus, described herein is a method of using a FEM to design an integrated modulation and compensation device that eliminates the need for multiple optical crystals. In certain embodiments, the FEM is used to optimized the integrated modulation and compensation device for noninvasive glucose-monitoring applications. As described in the examples herein, a 3D FEM was developed in order to predict the magnetic fields caused by various inductive coils in order to custom-design an IFMC system for noninvasive glucose sensing applications.

EXAMPLES

Example 1

Building a FEM and Testing an IFMC System

A FEM was designed for accurate and efficient field calculations in both compensator and modulator coils, such that magnetic fields caused by the inductive currents could be determined for a wide range of off-the-shelf inductors. The results were used to select specific coils to be implemented in a modular IFMC system based on the requirements of a noninvasive physiological glucose sensor of 1° modulation depth and 0.0632° for maximum compensation depth.

Figure 5B:
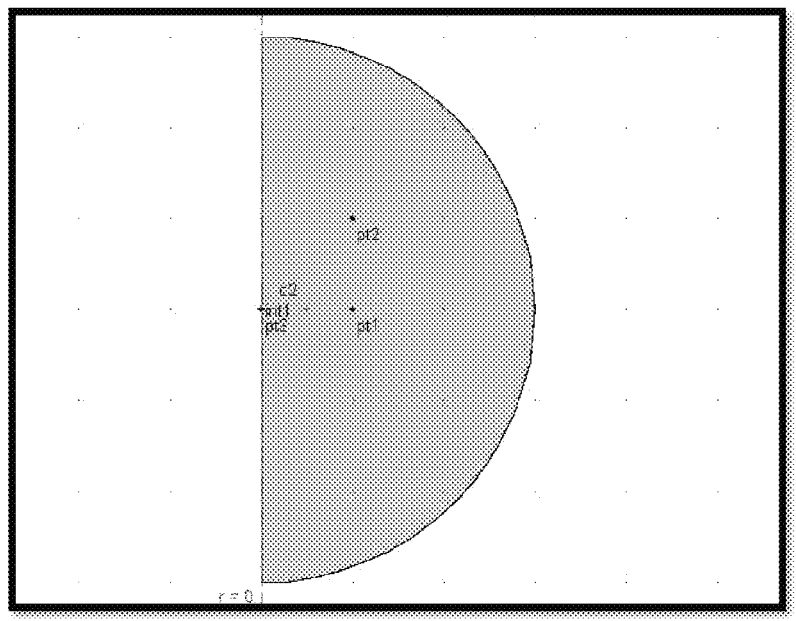
FIG. 5B: Schematic illustration of a single loop geometry as shown with two-dimensional axial symmetry around the r-axis where the grey region represents the boundary region (200 mm radius half-circle). The various points represent analysis points while the wire cross-section is 5 mm from the origin.

The FEM was designed using the AC/DC Module in COMSOL® Multiphysics (COMSOL, Inc., Burlington, Mass.). To begin, a model was created based on the geometry of FIG. 5A, which represents a single loop of current using the 2D axisymmetric dimension scheme, the magnetic fields physics selection, and the stationary solver sequence. A single loop of current with a radius of 5 mm and a magnitude of 71 mA was evaluated using the Biot-Savart Law in a stationary analysis. A cross section of the loop of wire was drawn 5 mm away from the rotational axis and was assigned as a single-turn coil domain with an initial vector potential of zero, the conductivity of copper, and an applied current of 0.0701 A. Then, the material properties of air were defined within the boundary region (200 mm radius half-circle) and a free triangular mesh was applied to break the model into finite elements before launching the solver. With the loop centered at the origin around the z-axis, the selected analysis points were (0, 10, 0), (0, 10, 10), and (0, 0, 0), given in mm in the y-z plane and referenced as pt1, pt2, and pt3, respectively (as shown in FIG. 5B). The FEM resulted in a magnetic field at these points of magnitude 7.57 mG, 3.02 mG, and 88.11 mG, respectively. After solving the FEM, equations representing the magnetic field from a single, uniform loop of current at any point in space were solved in Mathcad (PTC, Needham, Mass.) with the same initial conditions at various points in space in order to compare the FEM with the mathematical model.

FIG. 5B displays an image of the single loop geometry shown with 2D axial symmetry around the r-axis. The process was then repeated for a three-loop coil domain in COMSOL® and using superposition of the Biot-Savart model for three different loops. Table 1 displays the calculated error between the FEM and the Biot-Savart Law.

TABLE 1

Initial 2D FEM-predicted magnetic field results as compared to the Biot-Savart Law calculations

| | Single Loop Analysis | | | Triple Loop Analysis | | |
|---|---|---|---|---|---|---|
| Coordinate Point (mm) | FEM (mG) | Biot-Savart (mG) | Error (%) | FEM (mG) | Biot-Savart (mG) | Error (%) |
| (0, 10, 0) | 7.57 | 7.60 | 0.39 | 22.75 | 22.76 | 0.04 |
| (0, 10, 10) | 3.02 | 3.03 | 0.33 | 9.04 | 9.10 | 0.66 |
| (0, 0, 0) | 88.11 | 88.09 | 0.02 | 264.13 | 264.03 | 0.04 |

Figure 6A:
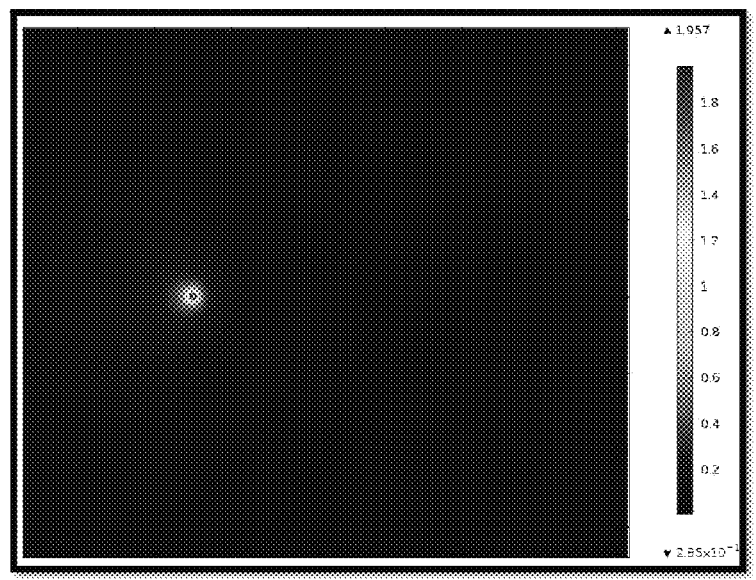
FIGS. 6A-6B: Color map magnitude plot given in Gauss (FIG. 6A), and streamline direction plot (FIG. 6B) of the magnetic field from a FEM analysis of a single loop of current.
Figure 6B:
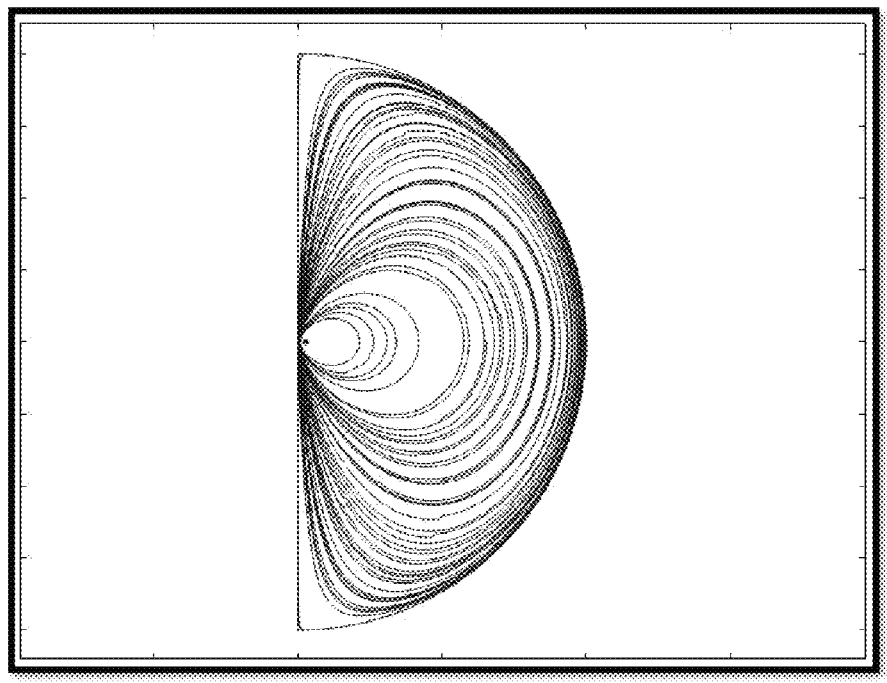
Figure 7A:
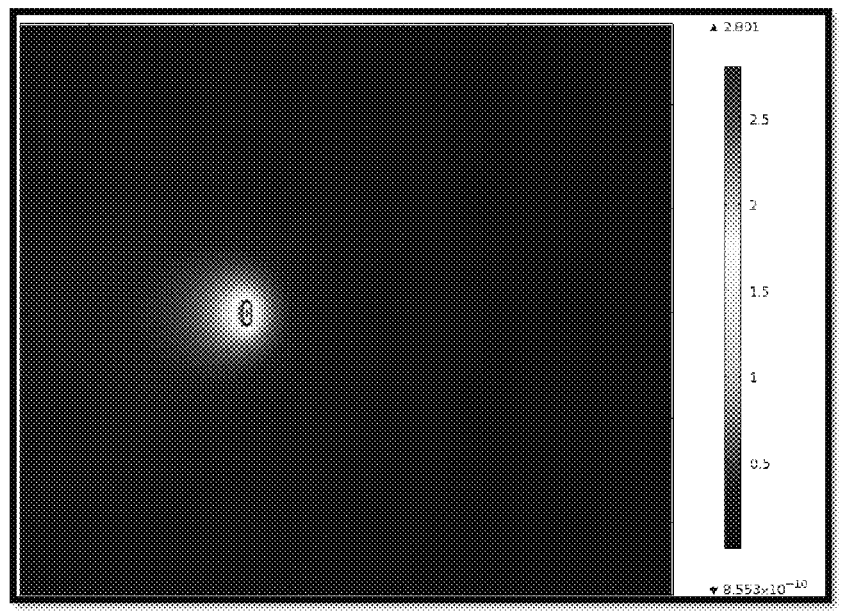
FIGS. 7A-7B: Color map magnitude plot given in Gauss (FIG. 7A), and streamline direction plot (FIG. 7B) of the magnetic field from a FEM analysis of three loops of current.
Figure 7B:
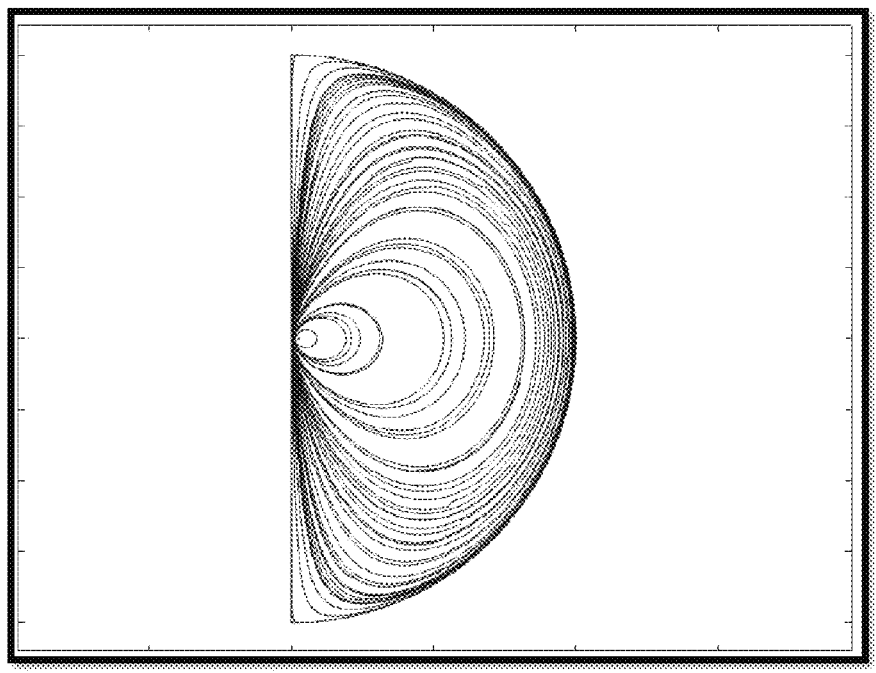

The FEM results are also shown in FIGS. 6A-6B, which show a concentration of field strength in close proximity to the coil (FIG. 6A) with field lines extending perpendicularly to the current direction (FIG. 6B). However, the field lines appear distorted around the boundary layer, indicating the need for an infinite element domain surrounding this boundary in order to resolve proper directionality. Furthermore, the total current-induced magnetic field at any point in space is the vector sum of all the individual contributions. Therefore, a simple sum of three identical current loops was also investigated. The FEM resulted in a magnetic field at pt1, pt2, and pt3 of magnitude 22.75 mG, 9.04 mG, and 264.3 mG, respectively. The Biot-Savart Law resulted in magnitudes of 22.76 mG, 9.10 mG, and 264.03 mG, respectively. Based on these results, the average error between the FEM and Biot-Savart Law was calculated to be 0.25%. These results are shown in FIGS. 7A-7B. These results demonstrate that there is a good correlation between the FEM prediction and the actual calculated value for inductive magnetic fields, establishing that the model can be used for more elaborate 3D coil configurations with the addition of an infinite element domain.

After the 2D axisymmetric FEM was related to the Biot-Savart Law calculations for a single loop and three loops of current, more complex 3D models were built and tested in COMSOL® to evaluate the magnetic field produced by different coils for use in Faraday compensation and modulation. In order to evaluate the models against physical rotational measurements, six ferrite core inductors of various size, shape, and inductance were purchased. The rated inductance of each coil used was 6.8 mH (PCH-45X-685_LT, Coilcraft, Inc., Cary, Ill.), 15 mH (PCH-27X-756_LT, Coilcraft, Inc., Cary, Ill.), 68 mH (DN4546-ND, Digi-Key Corporation, Thief River Falls, Minn.), 100 mH (PCH-45X-107_LT, Coilcraft, Inc., Cary, Ill.), 220 mH (M8397-ND, Digi-Key Corporation, Thief River Falls, Minn.), and 470 mH (M8397-ND, Digi-Key Corporation, Thief River Falls, Minn.). Prior to modeling the components, the inductance and impedance of each coil were measured using a digital multimeter (Beckman Industrial, Fullerton, Calif.), and the overall dimensions were measured with digital calipers (Mitutoyo, Aurora, Ill.).

Figures 8A, 8B:
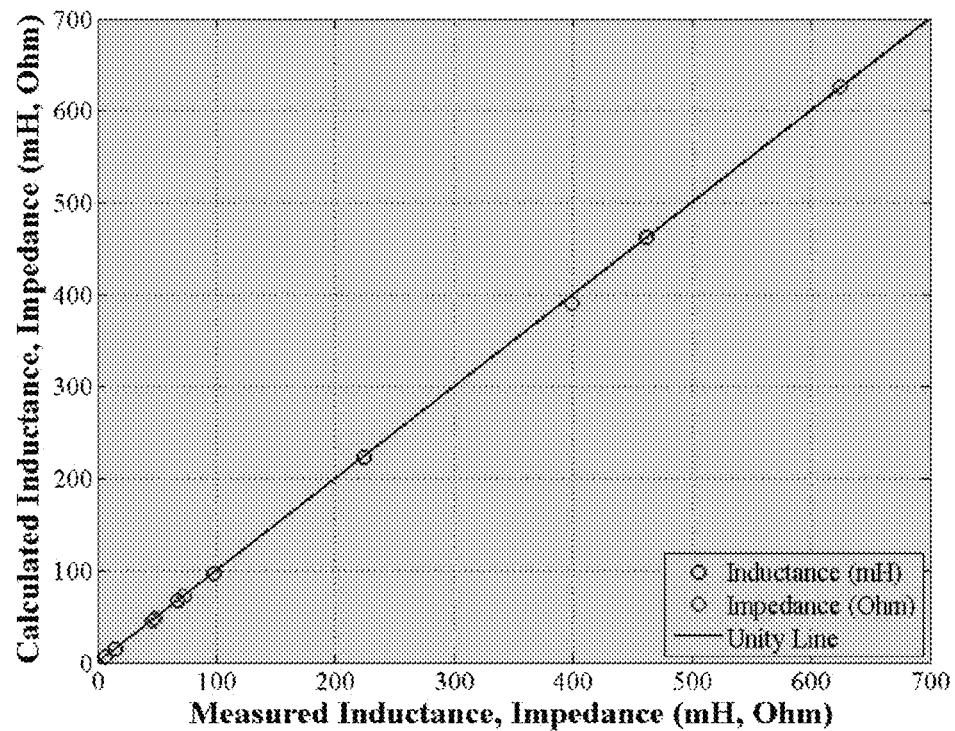
FIGS. 8A-8B: Graph (FIG. 8A) and table (FIG. 8B) displaying the error between measured and FEM values of inductance and impedance for each of six coiled devices.

A comparison of these values along with the associated errors can be seen in FIGS. 8A-8B. The average errors in inductance and impedance between the physical inductor and the FEM were 0.30% and 0.54%, respectively. Therefore, the models accurately represent the physical inductors under normal operating conditions.

Then, a 3D model of each coil was generated separately in COMSOL®, using the multi-turn coil domain feature and the parameters listed in the following Table 2 such that the measured parameters corresponded to the values within the model.

TABLE 2

Design parameters used to build each inductor within the FEM

| Inductor (mH) | 6.8 | 15 | 68 | 100 | 220 | 470 |
|---|---|---|---|---|---|---|
| Number of Turns | 407 | 875 | 1320 | 1591 | 2815 | 4110 |
| Wire Radius (mm) | 0.095 | 0.0365 | 0.059 | 0.053 | 0.0352 | 0.0352 |
| DC Voltage (VDC) | 1.62 | 3.89 | 2.92 | 5.91 | 10 | 10 |
| AC Source Voltage ($V_{rms}$) | 0.068 | 0.15 | 0.15 | 0.15 | 0.50 | 0.50 |
| AC Coil Voltage ($V_{pk}$) | 22.3 | 17.9 | 68.2 | 71.4 | 100 | 117 |
| Capacitance (µF) | 3.14 | 1.416 | 0.321 | 0.222 | 0.1056 | 0.0477 |
| Frequency (kHz) | 1.101 | 1.103 | 1.080 | 1.080 | 1.035 | 1.073 |

The geometry of the six inductors was built within COMSOL® so that they could be analyzed under both DC and AC conditions for magnetic field generation. Once the correct geometry was established for each coil, each geometry was implemented into a separate stationary FEM to evaluate the magnetic field potential in space when used as a compensator. In order to accurately represent how the coils would be physically tested in the stationary domain, modulation coils as well as the TDG rod were also modeled into the system due to the material properties and inherent mutual inductance between the modulator and compensator. This is desired because the signal has to be modulated in the physical system in order to take comparative measurements in rotation. However, it should be noted that the modulation coils were not active in this simulation as only the DC component was being measured. The modulation coils were only used to represent the surrounding materials within the test fixture. Three 100 mH inductors were selected to be used for modulation and they were oriented annularly, along with the compensator coil, around a TDG rod (13.5 mm long by 5.4 mm in diameter, MR32, Xi'an Aofa Optoelectronics Technology, Inc., Xi'an, China) at 90° intervals, based on a previously-made, 3D-printed fixture as shown in FIG. 3.

This orientation was selected to maximize the field generation along the axis of the TDG rod. The inclusion of these materials helps accurately represent the fixture that would be used for physical measurements, allowing for the necessary interactions to occur, such as mutual induction between coils.

Figure 9A:
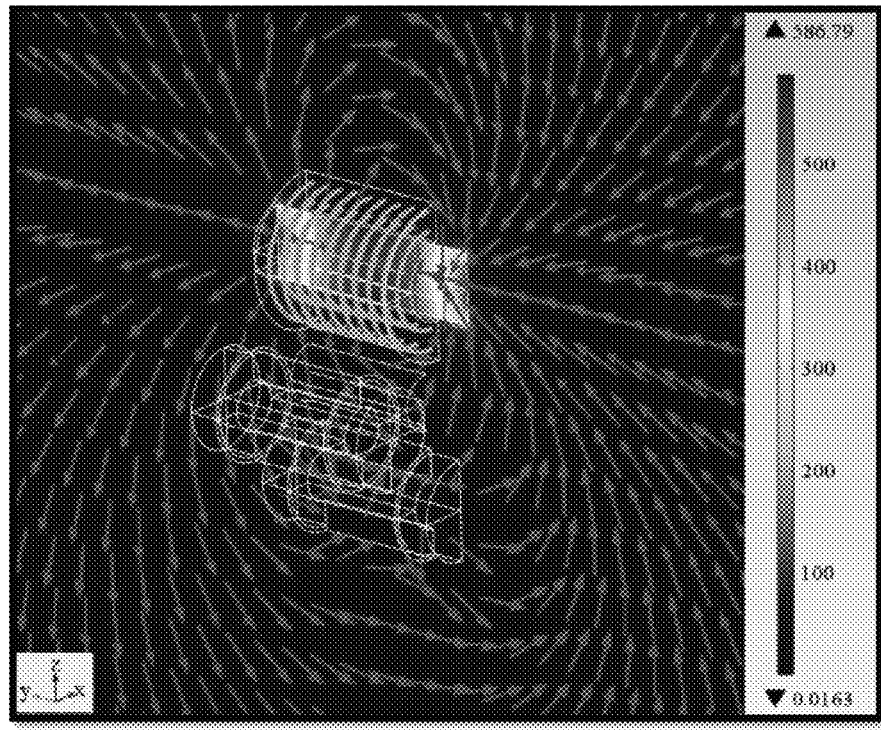
FIGS. 9A-9B: Three-dimensional color map plot of magnetic field (G) from a 470 mH inductor (FIG. 9A), and a two-dimensional plot of the axial component of the magnetic field through a terbium-doped glass (TDG) rod from each inductor (FIG. 9B) after stationary FEM analysis. The green curved lines in FIG. 9A represent the direction of current, and the red arrows represent the field direction.
Figure 9B:
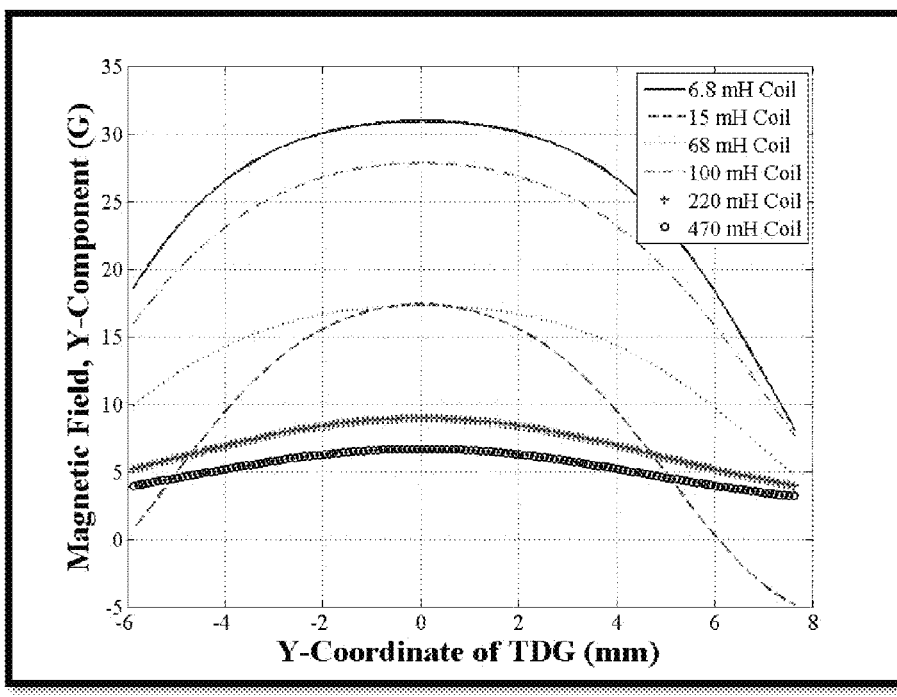

The models were then surrounded by a 100 mm (in radius) spherical air domain with a 50 mm thick infinite element shell domain to represent the analysis over all-space and eliminate distortion of field lines along the boundary layer. A 3D plot was created in COMSOL®, showing the magnetic field amplitude and the direction of the field lines as compared to current travel through the inductor. This plot, for the 470 mH coil, is shown in FIG. 9A. A second plot was created to visualize the axial component of the magnetic field along the length of the TDG rod. This plot is shown in FIG. 9B. From these plots, it can be seen that the magnetic field direction was perpendicular to the direction of current travel in the coil, and the largest B-field strength was localized within the magnetic core domain. Similar results were obtained from each coil, and the peak magnetic field was shown to occur along the middle of the inductor when y=0 mm. The offset in symmetry, shown in FIG. 9B, was due to the position of the TDG rod with respect to the coil, which was inherent to the fixture used in the physical system. Had the TDG rod been centered along the inductor, the resulting B-field plots would have been symmetric along the y=0 mm coordinate. It should also be noted that there was no overall relationship between individual inductors because they varied in size and shape. Furthermore, the results in FIGS. 9A-9B demonstrate the maximum B-field from each inductor, which represents a range of driving voltages based on the rated saturation current. These results can be averaged along the length of the TDG rod in order to predict the maximum compensation depth seen in polarized light with certain known parameters.

Once the geometry was complete, the material properties provided by COMSOL® were assigned to each domain as shown in Table 3, and the multi-turn coil domain was given the necessary parameters, such as wire conductivity, wire cross section, wire direction, and number of overall turns.

TABLE 3

Material properties input to the FEM as provided by COMSOL ®. The permeability of TDG was slightly increased compared to glass due to its magnetic properties

| Material Domain | Air | Ferrite Core | Copper Wire | TDG |
|---|---|---|---|---|
| Permeability | 1 | 2000 | 1 | 1.06 |
| Permittivity | 1 | 1 | 1 | 4.2 |
| Conductivity (S/m) | 0 | 0 | $5.96*10^7$ | $1*10^{-14}$ |

The material properties of glass were assigned to the TDG rod with a slight increase to relative permeability due to the magnetic properties of the material. Directionality of the current was determined using a built-in coil current calculation feature within the solver sequence, given a defined voltage input surface. Then, the initial vector potential was set to zero and the driving voltage was set so as to not exceed the saturation current of the coil in steady state while remaining below 10 VDC, which is the upper limit of the multifunction data acquisition device (DAQ; NI USB-6212, National Instruments, Austin, Tex.) that was used. The voltages used are listed in Table 2. Finally, a custom mesh was designed such that each component, as well as the spaces between, could be resolved (in order to produce an accurate solution) before the solver sequence was initiated. The results were then evaluated to show consistent magnetic field generation and the average axial component along the length of the TDG rod was calculated. This could then be correlated to an overall rotation in polarized light of a given wavelength, according to Equation 3. The results were used in comparison to physical rotational measurements in order to validate the model. This process was repeated for each coil under consideration.

Once the stationary results for each coil were established, a frequency domain analysis was performed in order to determine the maximum modulation depth. Each coil was evaluated in a similar FEM to determine the time-dependent magnetic field generation when used as a modulator. These models were created under the frequency domain solver sequence and contained only the coil of interest and the TDG rod, based on the orientation used for physical measurements, as shown in FIG. 3B. These models implemented the individual coil and TDG rod geometry without extra modulation coils in order to reflect the orientation of the physical fixture. This orientation did not require other coils to be modeled for modulation because the purpose of the simulation was to measure the modulation from a single coil, rather than to provide a DC offset component in the presence of modulation.

These models were also assigned with A-field gauge fixing in the magnetic field domains, which was important in order to reach a stable solution within the frequency solver sequence. This provides an additional variable for potential and its affiliated conservation equation. A capacitance was calculated such that signal resonance could be achieved at a frequency between 1.0 and 1.1 kHz when driven with a sinusoidal source. Then, each model was driven with a capacitive load at its resonant frequency based on physical system measurements and the coil values given in Table 2. The model was setup to run at the selected frequency with a maximum AC voltage across the coil of a magnitude that would prevent current saturation. The results were then used to calculate the modulation depth along the length of the TDG rod, and the overall power consumption was determined. The steady state results are displayed in FIGS. 10A-10B.

Figure 10A:
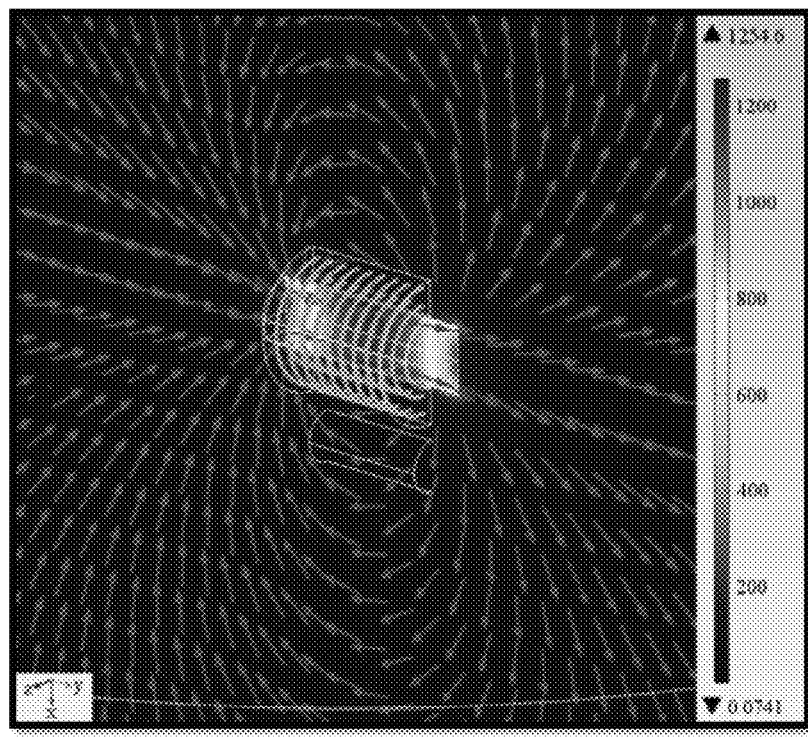
FIGS. 10A-10B: Three-dimensional color map plot of magnetic field (G) from a 470 mH inductor (FIG. 10A), and a two-dimensional plot of the average axial component of the magnetic field through the TDG rod with respect to the phase angle of the driving source from each inductor (FIG. 10B) after frequency domain FEM analysis. The green curved lines in FIG. 10A represent the direction of current, and the red arrows represent the field direction.
Figure 10B:
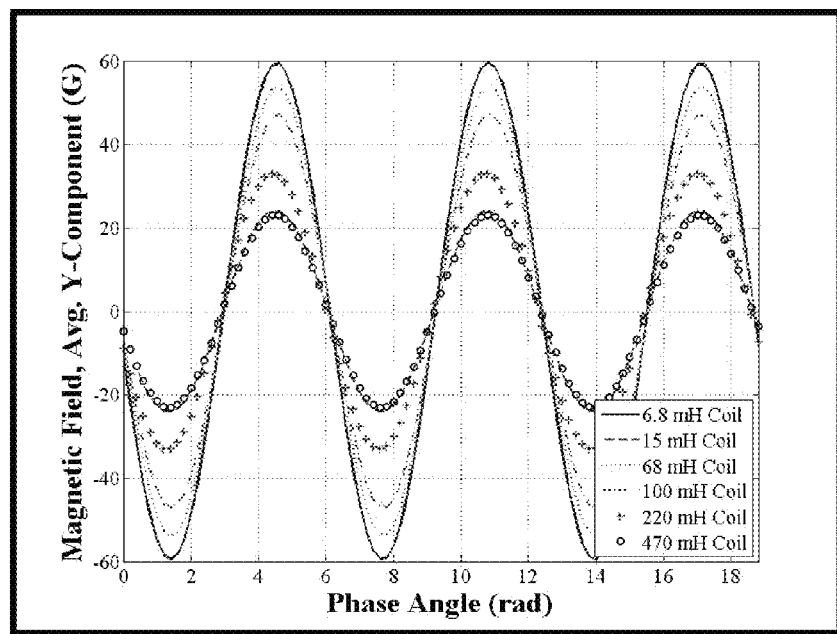

The results from the 470 mH inductor are shown in a 3D color map plot in FIG. 10A. FIG. 10B shows a 2D plot of the average axial magnetic field component along the length of the TDG rod with respect to the phase angle of the driving source. The plot in FIG. 10B displays the maximum results from each coil. Again, it can be seen that the magnetic field direction is perpendicular to the current travel, and the field intensity follows a sinusoidal path dependent on the frequency of the voltage source. These results show no overall relationship between individual inductors due to the same reasons described for the compensator models. However, the peak results can be used to predict the maximum modulation depth seen in polarized light, given certain known parameters.

Figure 11A:
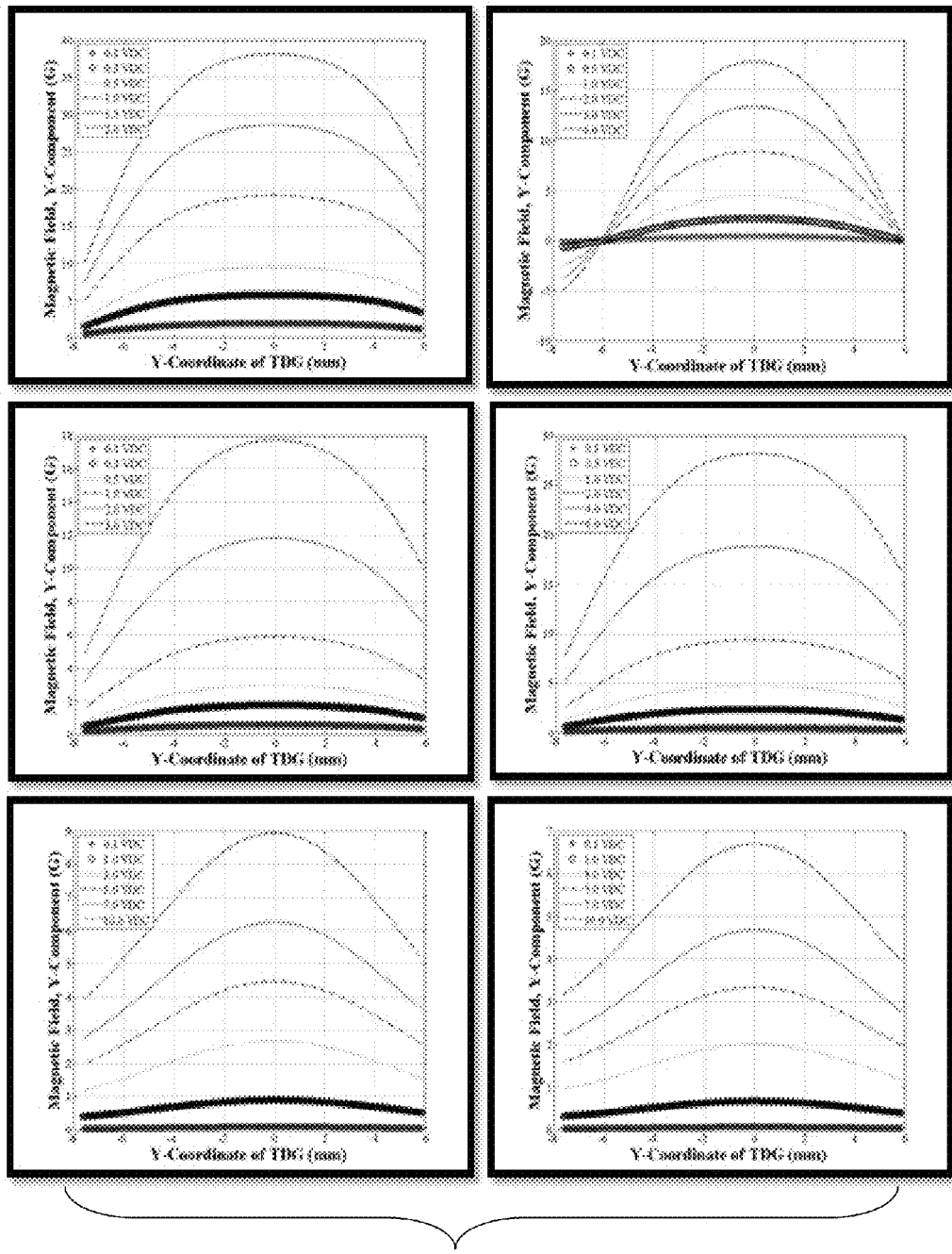
FIG. 11A: A series of graphs showing FEM parametric voltage sweep results from each coil in compensation. Starting with the upper left plot and proceeding from left to right, top to bottom: 6.8 mH coil, 15 mH coil, 68 mH coil, 100 mH coil, 220 mH coil, and 470 mH coil.
Figure 11B:
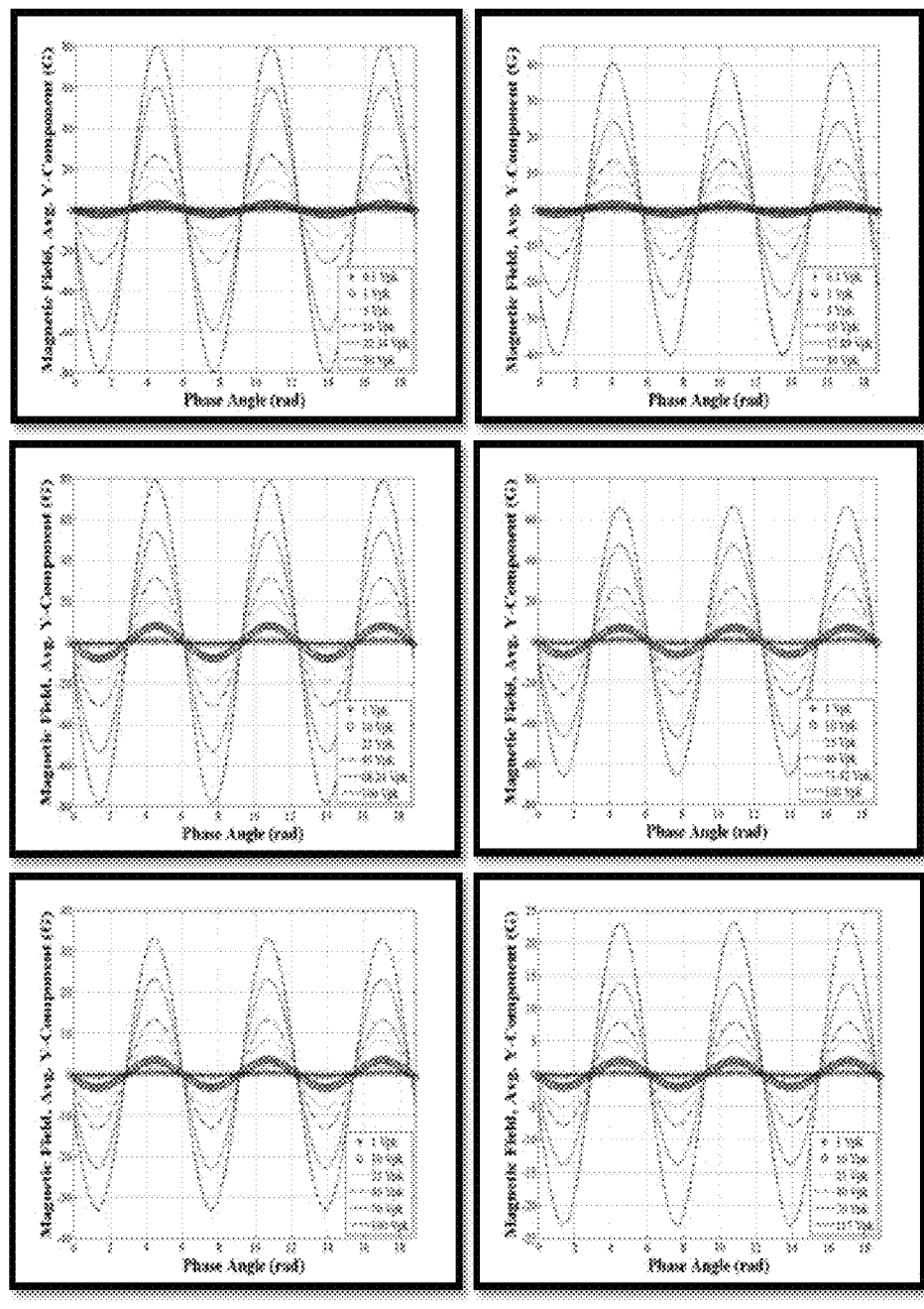
FIG. 11B: A series of graphs showing FEM parametric voltage sweep results from each coil—in modulation. Starting with the upper left plot and proceeding from left to right, top to bottom: 6.8 mH, 15 mH coil, 68 mH coil, 100 mH coil, 220 mH coil, and 470 mH coil.

Once the compensation and modulation depths of each coil were established, they were compared to physical measurements in order to validate the accuracy of the FEM. Finally, once a model was developed for each coil in compensation and modulation, a parametric sweep was run on each model in order to obtain a relationship between magnetic field strength and driving voltage. Each model was tested over a linear voltage range below the maximum rated value in both compensation and modulation. The results from each coil in compensation and modulation are shown in FIG. 11A and FIG. 11B, respectively. These results indicate that the different size, shape, and inductance of each coil provide a unique operational range of rotations based on the maximum voltage.

Figure 12A:
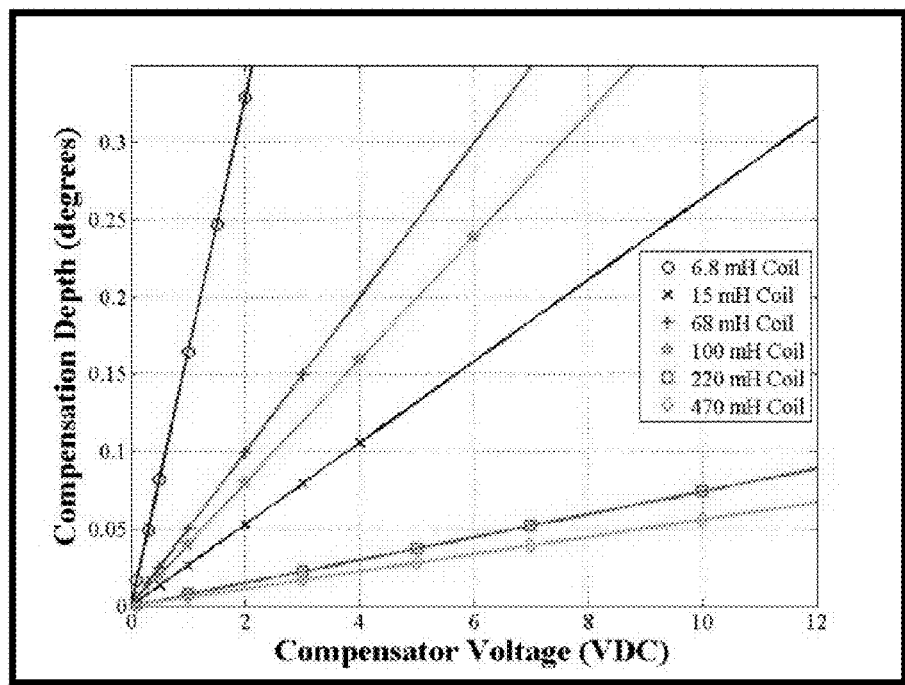
FIGS. 12A-12B: Graphs showing the relationship between compensation depth and driving voltage (FIG. 12A), and modulation depth and driving voltage (FIG. 12B), for each inductor based on FEM results.
Figure 12B:
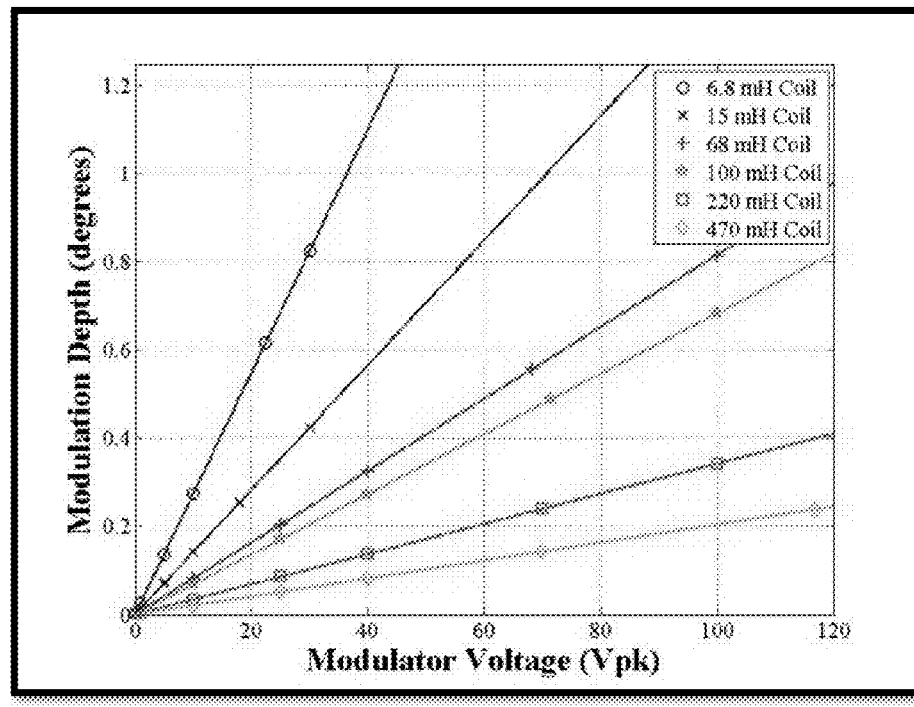

It should also be noted that, in certain embodiment, the 15 mH coil should not be used in such Faraday-based polarimetric applications because of the variation in sign of the magnetic field along the length of the TDG rod. Due to the short length of the coil, a portion of the magnetic field along the length of the TDG rod was negative, meaning that it will work against itself to achieve a collective rotation in one direction. However, the magnetic field results from each coil were averaged and used to calculate Faraday rotation based on the driving voltage. The plots which relate rotation to driving voltage can be seen in FIGS. 12A-12B. These results demonstrate a linear relationship between rotation and voltage in both compensation and modulation within the operational range of each inductor. Plots such as these are useful for selecting the necessary driving voltage in order to achieve a required rotational depth in polarimetric systems with specific inductors. Given that the lines pass directly through zero, the slope can be used for making these predictions.

Figure 13A:
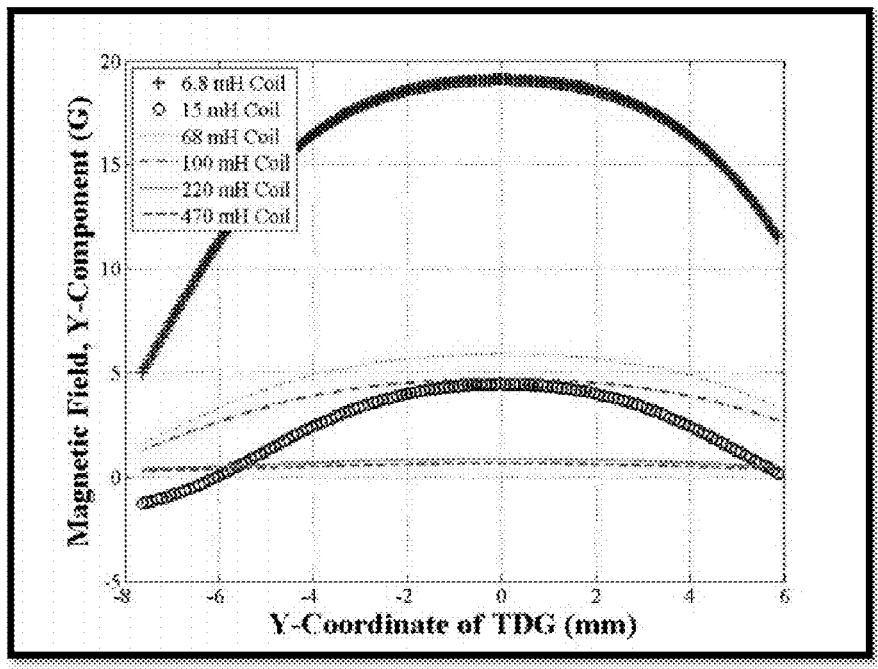
FIGS. 13A-13B: Graphs showing FEM results comparing each coil—in compensation while being driven with a 1 VDC source (FIG. 13A), and in modulation while being driven with a 10 $V_{pk}$ source (FIG. 13B).
Figure 13B:
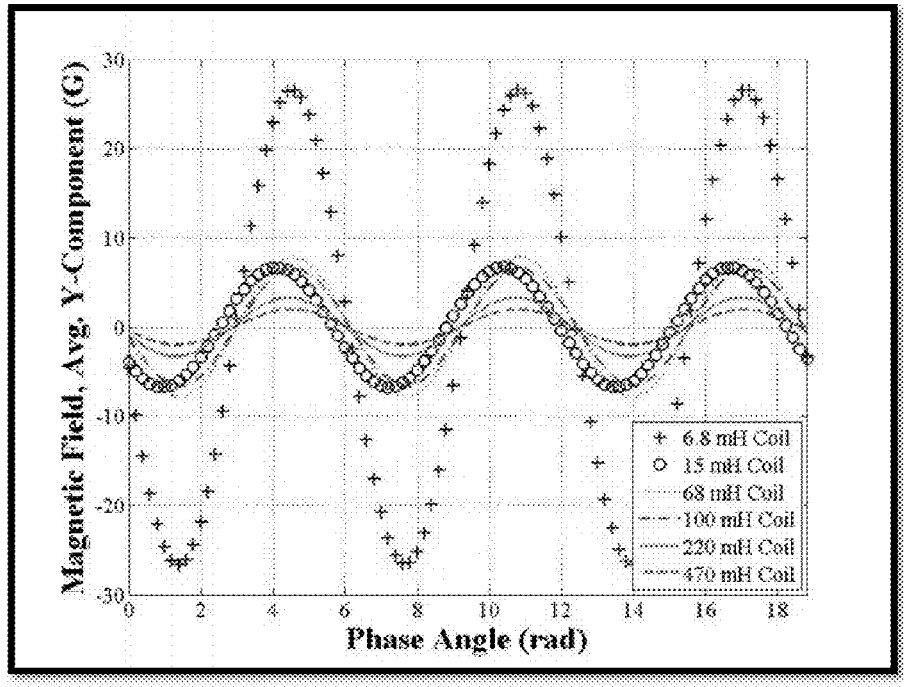

The voltage sweep results were utilized to provide a comparison in magnetic field strength between each inductor when driven with a common voltage source, as depicted in FIGS. 13A-13B. The 1 VDC results were compared between coils in compensation and the 10 $V_{pk}$ results were compared between the coils in modulation. These results indicate that there was an inverse relationship between inductance and field strength. The exception to this rule is shown to be the 15 mH coil. Without wishing to be bound by theory, this exception is likely due to the smaller size as compared to the other five coils. Generally, coils with a higher inductance are manufactured with more turns of wire, producing larger resistances, and reducing the amount of current that can flow through the inductor. Although these coils have more turns, which also affect the total magnetic field generated, the larger resistance is the limiting factor. Therefore, in order to produce larger Faraday rotations, coils with lower inductances should be used. Then, the linear relationship between rotation and voltage can be used to pinpoint the exact rotation needed in a given application.

Figure 14:
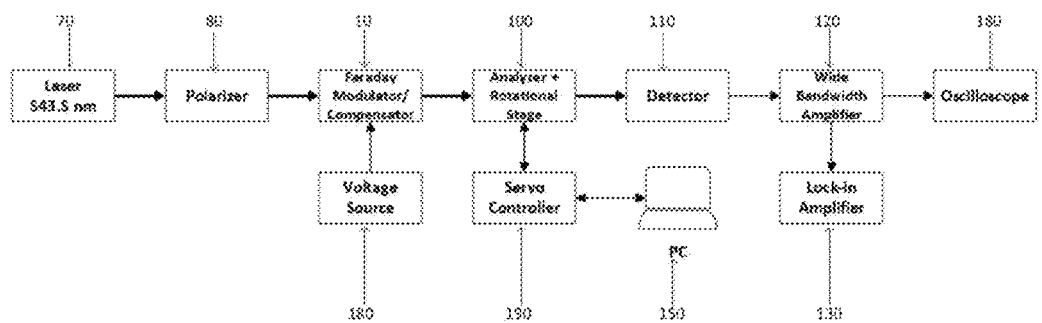
FIG. 14: Schematic illustration of an IFMC system used to measure Faraday rotations (both modulation and compensation). The thick lines represent the path of light whereas the thin lines represent electrical communication.

After the FEM was used to predict rotational measurements, each coil was physically tested to measure modulation depth in a standard polarimeter as depicted schematically in FIG. 14. The test system utilized a 5 mW, 543.5 nm HeNe laser (CVI Melles Griot, Albuquerque, N. Mex.) as the light source 70, which passed through a linear polarizer (Newport, Irvine, Calif.) 80 with a vertically oriented polarization plane. The polarized signal proceeded through a 1.35 cm-long TDG rod (MR32, Xi'an Aofa Optoelectronics Technology, Inc., Xi'an, China) before traveling through the analyzer 100, consisting of a second linear polarizer (Newport, Irvine, Calif.) with a horizontally oriented polarization plane. The analyzer 100 was mounted to a rotational stage controlled through a DC servo motor controller (Thorlabs, Newton, N.J.) 190 attached to a PC (Dell, Round Rock, Tex.) 150 running the manufacturer's servo control software. The final signal was detected with a high speed Si photodetector (Thorlabs, Newton, N.J.) 110 and amplified with a wide bandwidth amplifier (CVI Melles Griot, Albuquerque, N. Mex.) 120. The inductor was oriented parallel to the TDG rod, matching the orientation used in the FEM. Prior to testing the coil, a series capacitance was chosen using off-the-shelf Mylar capacitors to achieve resonance at a frequency between 1.0 and 1.1 kHz.

Once the circuit was assembled, it was driven with the sinusoidal reference output of a lock-in amplifier (Stanford Research Systems, Sunnyvale, Calif.) at resonance and a maximum permitted inductor voltage based on the saturation current of the coil through a custom power amplifier (Marchand Electronics Inc., Rochester, N.Y.) with a gain of 40 V/V. The detected signal was observed visually on an oscilloscope (Agilent, Santa Clara, Calif.), and input back to the lock-in amplifier.

Once the inductive circuit was energized, the analyzer was rotated such that the $2\omega_m$ component was dominant and the lock-in output was zero. Then, the angular position of the analyzer was recorded, the stage was rotated until the $2\omega_m$ signal was eliminated, and the final angular position was recorded. The change in rotation represents the total modulation depth for a given inductor, driving voltage, and orientation when the polarizer and analyzer were initially crossed, and the detected output was centered around zero. The $2\omega_m$ signal was completely eliminated when the analyzer had rotated just enough so that the peak of the modulated signal no longer crossed the null plane of the analyzer, and the detected signal was of the same frequency as the reference signal ($\omega_m$). This process was carried out in triplicate and averaged for each coil before comparing values to the FEM output. The averaged results of measured rotation versus the FEM-calculated rotation were plotted in MATLAB, as shown in the right side of FIG. 16.

The standard deviation of the residuals of the rotational data based on these measurements was then calculated to determine a prediction error between measurements and the FEM calculations. The error in prediction of modulation was calculated to be 0.0044°, which is 0.71% of the largest rotation seen in the data. Therefore, the developed FEM can accurately predict the depth of Faraday modulation for various off-the-shelf inductors.

After the modulation depth of each coil was measured, a similar process was used for measurement of the maximum compensation depth that each coil was capable of achieving with the addition of a modulation component to be used for signal detection, when driven with a DC voltage source. Modulation was necessary due to the sensitivity required for measuring millidegree polarization rotations. The same polarimeter system described above was used with the addition of the modulation component, which consisted of three 100 mH coils, surrounding the TDG rod as shown in FIG. 3A, and a 0.0823 µF series capacitance. Once the system was assembled into the test fixture, the modulator was driven with a 20 $V_{rms}$ sinusoidal signal at a frequency of 1.1 kHz, and the analyzer was rotated until the lock-in output was zero. Then, the angular position was recorded, and the compensator was powered with a DC power supply (Hewlett-Packard Company, Palo Alto, Calif.) with the same inductor voltage used in the equivalent FEM so as to avoid current saturation and avoid exceeding the 10 VDC limit of the DAQ. The analyzer was rotated again until the lock-in output was zero and the $2\omega_m$ signal was dominant before recording the final angular position. The total rotation represents how far from the null plane that the compensator coil caused the signal to rotate based on the Faraday effect. This process was also carried out in triplicate and averaged for each coil before comparing values to the equivalent FEM output.

Figure 16:
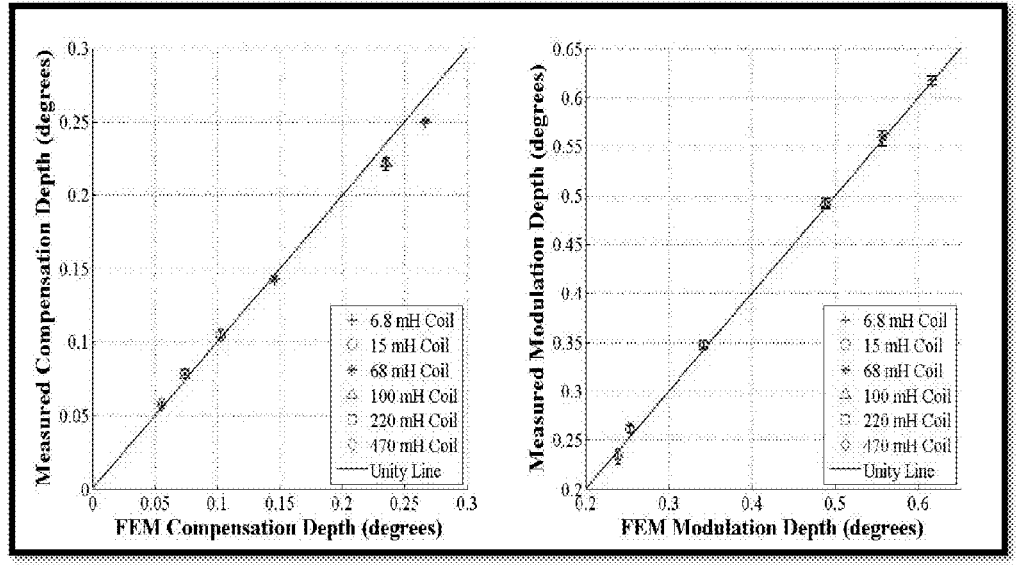
FIG. 16: Graphs showing prediction error in compensation (left) and modulation (right) between FEM analysis and the physical measured values.

The results of measured rotation versus the FEM-calculated rotation was plotted in MATLAB, as shown in the left side of FIG. 16. Based on these results, the error in prediction of compensation was calculate to be 0.0087°, which is 3.26% of the largest rotation seen in the data series. Although this was higher than the modulator prediction error, it was still within reasonable accuracy for successful compensator prediction and coil selection. Without wishing to be bound by theory, it is believed the primary source of this error was due to the difficulty of measuring angles with sub-millidegree sensitivity, rather than general discrepancies within the FEM. Using a mechanical rotational stage for measuring polarization angles of this magnitude was reasonable but still produces inherent error. Also, the placement of the coil with respect to the TDG rod largely affects the rotational results, meaning that any slight difference between the fixture and the FEM geometry could also produce error. However, it was demonstrated that the overall model provides an accurate representation of the physical system.

Example 2

Optimization of the IFMC System to Predict Physiological Glucose Concentrations

The results above demonstrate that the FEM successfully predicts Faraday rotation in both compensation and modulation components in a polarimetric system. Because a commercial noninvasive glucose sensor would benefit the diabetic community by offering an accurate alternative to the current invasive means of detection, saving costs in health, and improving overall patient health and compliance, the IFMC system was configured for use in the noninvasive polarimetric sensing of glucose. The primary size and cost factor in these systems has been the separation of Faraday modulation and compensation components, which as discussed above previously needed multiple optical rods and custom-built inductive coils.

A typical physiological glucose detection system may have to sense blood glucose concentrations as high as 600 mg/dL under hyperglycemic conditions. Given the specific rotation of D-glucose, a polarimetric-based system would need to be able to resolve a range of rotation between 0 and 63.2 millidegrees, given a 1 cm path length (characteristic of the aqueous humor of the eye, where noninvasive sensing is likely to take place), a source wavelength of 543.5 nm, and a worst-case concentration of 1000 mg/dL. Therefore, an effective Faraday compensator component should obtain a rotation of at least 0.0632° so as to fully encompass this range. Similarly, an effective Faraday modulator should obtain a modulation depth of at least 1°, which is much larger than the maximum rotation that may occur due to glucose.

Figure 17:
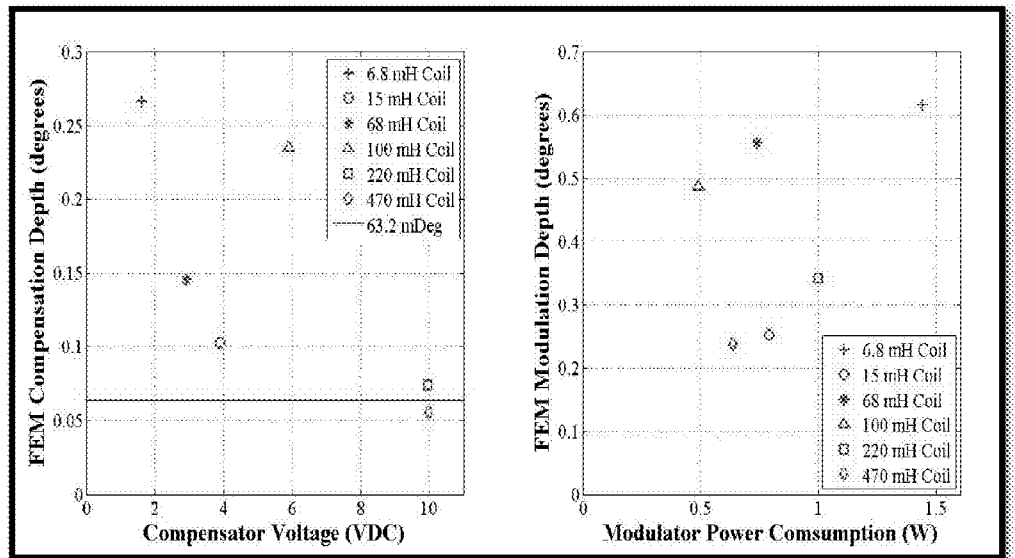
FIG. 17: Graphs showing maximum compensation depth versus driving voltage (left), and maximum modulation depth versus average power consumption (right), for different inductors based on the FEM output. The horizontal blue line on the left plot indicates the minimum rotational requirement necessary for successful physiological glucose measurements. The minimum rotational requirement for a physiological glucose sensor is presented as the blue horizontal line on the plot on the left. Points on the upper-left side of the plot on the right represent the highest rotation-to-power ratio (RTPR).

To design the IFMC system, the maximum FEM data from Example 1 was plotted in MATLAB, as shown in FIG. 17. These plots were used to select the optimal coils for device design. The plots represent compensation depth versus driving voltage (left) as well as modulation depth versus average power consumption (right). These types of plots are useful for selecting a compensator coil to be used in an IFMC system when a minimum rotation is needed and there is a maximum voltage allotted by the driving electronics. The minimum rotational requirement for a physiological glucose sensor is presented as the blue horizontal line on the plot on the left of FIG. 17. These plots are also useful for selecting a modulator configuration to be used in an IFMC system when a minimum depth must be achieved while maintaining low power. Points on the upper-left side of the plot on the right of FIG. 17 represent the highest rotation-to-power ratio (RTPR).

Figure 18A:
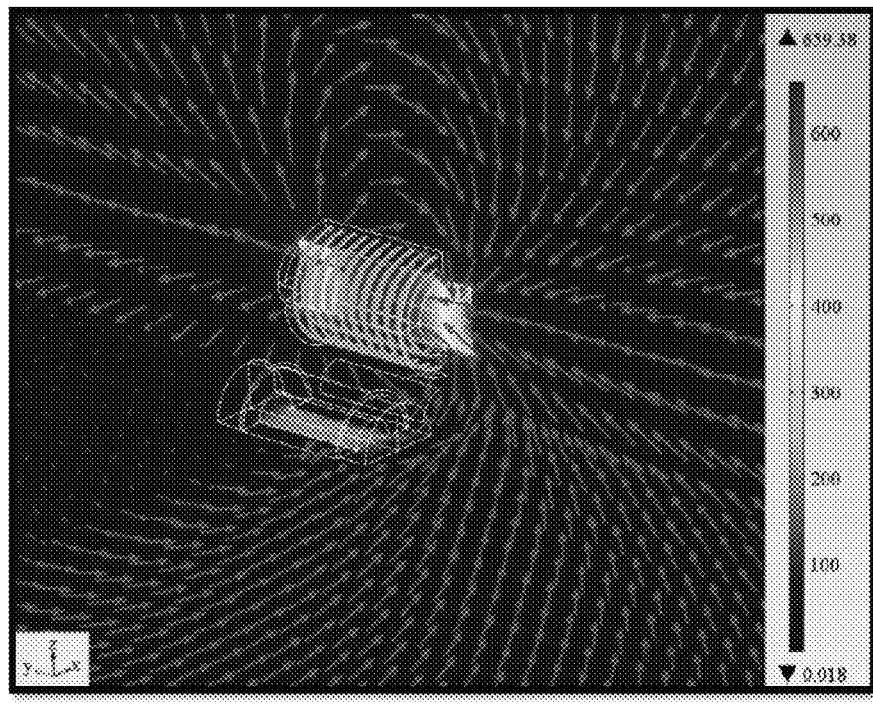
FIGS. 18A-18B: Three-dimensional color map plot of magnetic field (G) of the IFMC system in compensation (FIG. 18A) and modulation (FIG. 18B) after FEM analysis. The green curved lines represent the direction of current, and the red arrows represent the field direction.
Figure 18B:
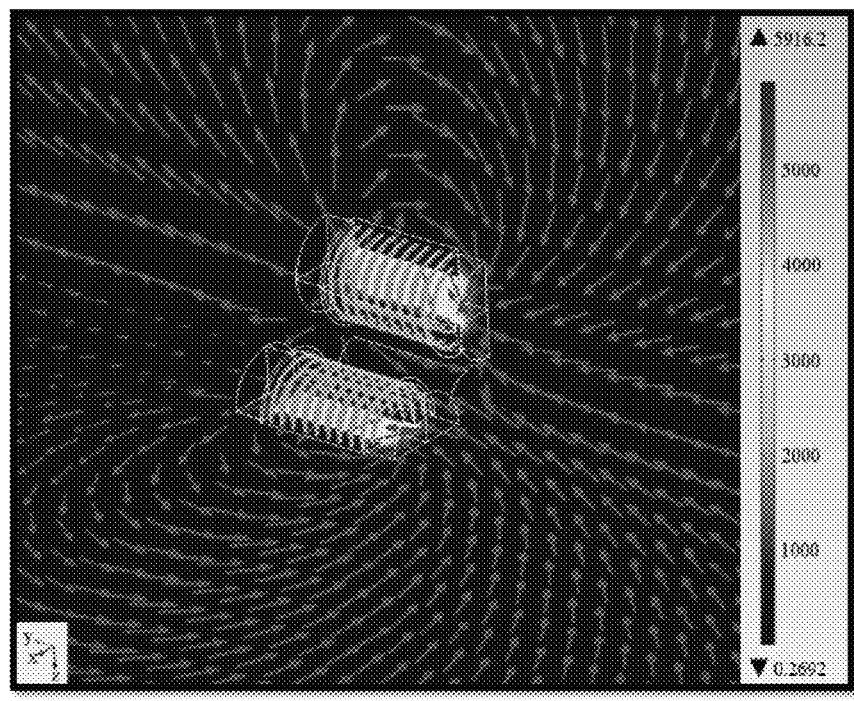

The coil selected to operate as the compensator was the 220 mH inductor because it was able to achieve a rotation of 0.0740°, which is larger than the minimum requirement of 0.0632° and it can utilize the full 10 VDC range of the DAQ used in feedback control. Due to the fact that no single coil was able to achieve a modulation depth larger than 1°, three 100 mH coils connected in series were selected to operate as the modulator component. These coils were selected because they produce an individual modulation depth of 0.4881° and have the highest RTPR of 0.9961°/W. Once the coils were selected, a FEM was built to reflect the properties of the coils, surrounding the parallel TDG rod. Initially, a stationary analysis was computed with a 10 VDC source applied to the 220 mH coil in order to predict the maximum possible compensation depth. Then, a frequency domain analysis was computed with a 45 $V_{rms}$ sinusoidal source at a frequency of 1.073 kHz applied to each 100 mH coil. These resulted in a total compensation depth of 0.0780° and modulation depth of 1.2404°, indicating that both requirements were successfully met by the IFMC system. The average power calculated for the modulation circuit was 1.99 W, which produces a RTPR of 0.6233°/W. The decrease in this figure when compared to individual 100 mH coils was due to the mutual induction losses between coils, which also explains why the total modulation depth was not simply three times as large as the depth produced by a single coil. A 3D color map plot of the IFMC system in compensation and modulation from COMSOL® is shown in FIGS. 18A-18B. Both images indicate the expected interaction between coil currents and magnetic field, which further supports the FEM.

The DC axial component of the magnetic field was averaged along the length of the TDG rod and the corresponding rotation was calculated. Next, the total inductance and impedance was measured and a capacitance was calculated such that signal resonance would occur at a frequency between 1 and 1.1 kHz when drive with a sinusoidal voltage source based on Equation 16:

$$2\pi f = \frac{1}{\sqrt{LC}}$$ Equation 16 where f is the frequency, L is the inductance, and C is the capacitance. The calculated capacitance was also attached in series with the modulator coils. Circuit analysis was conducted to determine the voltage drop across each coil when driven with a 20 $V_{rms}$ signal at resonance. Finally, these parameters were assigned to the modulator coils within the FEM such that current would travel in the same direction around each coil, and the frequency domain study was computed. The results were used to determine the AC axial component of the magnetic field along the length of the TDG rod, and the corresponding modulation depth was calculated.

Once the FEM indicated that the IFMC system meets the design requirements, a physical IFMC system was produced using three serially connected 100 mH inductors as the modulator and one 220 mH inductor as the compensator. The four coils were assembled to replicate the FEM, and fixed in a custom, hand-held housing that was designed in SolidWorks® system (SolidWorks Corporation, Waltham, Mass.) and fabricated with a 3D printer (Objet, Rehovot, Israel) as shown in FIG. 3.

Within the housing, the coils were oriented parallel and annularly at 90° intervals around a TDG rod (13.5 mm long by 5.4 mm in diameter). The three modulator coils were connected in series such that current would flow in the same direction around each coil, producing a collectively maximized axial component of the magnetic field along the TDG rod which is important for effective Faraday modulation. All electrical connections were soldered together. The terminals for the compensator and modulator were attached to a 6-pin mini circular connector (illustrated in FIG. 3 as 52), and mounted to the external surface of the housing. Standard 30 mm optical cage mounts and ¼-20 threaded post mounts were used for easy integration with standard optical equipment. Also, the interior was designed such that different inserts would allow for a variety of off-the-shelf inductors to be used at various distances from the centered TDG rod, providing a universal kit for a wide range of different polarimetric applications. The final design was then integrated with the polarimetric system used for rotational measurements, and the total compensation and modulation depths were determined After the final assembly was coupled to the polarimetric system, it was tested to measure modulation and compensation depth. Once the system was fully assembled, the modulator produced a measured inductance of 245 mH and an impedance of 201Ω. Therefore, a total capacitance measuring 0.0898 μF was serially connected to the modulator coils in order to achieve signal resonance at a frequency of 1.073 kHz when driven with a sinusoidal voltage source. The final assembly produced a modulation depth of 1.2226° when driven with a 20 $V_{rms}$ sine wave at 1.073 kHz, producing a measurement error of 1.44%. The compensator coil produced a measured inductance of 227 mH, an impedance of 358Ω, and an average rotation of 0.0794° when excited with a 10 VDC source, producing a measurement error of 1.70%. Therefore, the IFMC system is capable of meeting the minimum requirements of 0.0632° in compensation and 1° in modulation for successful physiological glucose detection. Furthermore, the overall error associated with the IFMC system demonstrates that a FEM can be used to successfully design and optimize the components within a specific polarimetric application.

Example 3

Validation of an IFMC System

The IFMC system was validated under two separate conditions. First, static measurements were taken to formulate a calibration model and calculate errors in prediction. Second, a dynamic flow system was designed to control glucose concentrations in real time so that measurements could be taken continuously. Accordingly, the IFMC system was tested in a polarimetric system against glucose-doped water in a static sample cell and a dynamic flow system programmed with a physiological glucose profile.

The IFMC system of Example 2 was validated using a single wavelength digital closed-loop polarimeter. The system utilized a 5 mW, 543.5 nm HeNe laser (CVI Melles Griot, Albuquerque, N. Mex.) as the light source, which passed through a linear polarizer (Newport, Irvine, Calif.) with a vertically oriented polarization plane. The polarized signal then proceeded through a custom sample cell with a 1 cm path length before traveling through the IFMC system. Finally, the modulated signal was passed through an analyzer consisting of a second linear polarizer (Newport, Irvine, Calif.) with a horizontally oriented polarization plane, before being detected with a high speed Si photodetector (Thorlabs, Newton, N.J.) and amplified with a wide bandwidth amplifier (CVI Melles Griot, Albuquerque, N. Mex.). The modulator was driven with the sinusoidal reference output of a lock-in amplifier (Stanford Research Systems, Sunnyvale, Calif.) at a voltage of 0.5 $V_{rms}$ and a frequency necessary for achieving signal resonance through a custom power amplifier with a gain of 40 V/V (Marchand Electronics Inc., Rochester, N.Y.). The detected signal was input to the lock-in amplifier and observed visually on an oscilloscope (Agilent, Santa Clara, Calif.). The output from the lock-in amplifier was captured by a multifunction data acquisition device (DAQ, National Instruments, Austin, Tex.) and read on a PC (Dell, Round Rock, Tex.). The information was processed in a PID continuous feedback VI created in Lab VIEW (National Instruments, Austin, Tex.). The feedback loop controlled a voltage buffer circuit powered with a DC power supply (Hewlett-Packard Company, Palo Alto, Calif.) through the DAQ which would apply a DC voltage to the compensator coil in order to align the polarized signal perpendicularly to the analyzer by magnetic field generation, centering the modulated signal on the null plane, and producing a detected signal with a frequency of twice the reference signal. This applied voltage was proportional to any rotation in the polarized signal that would occur within the system, such as that due to glucose within the sample cell. Therefore, the output from the PID controller could be directly used to predict the glucose concentration in unknown samples of fixed path length with a linear calibration model.

Static Glucose Detection

Figure 15:
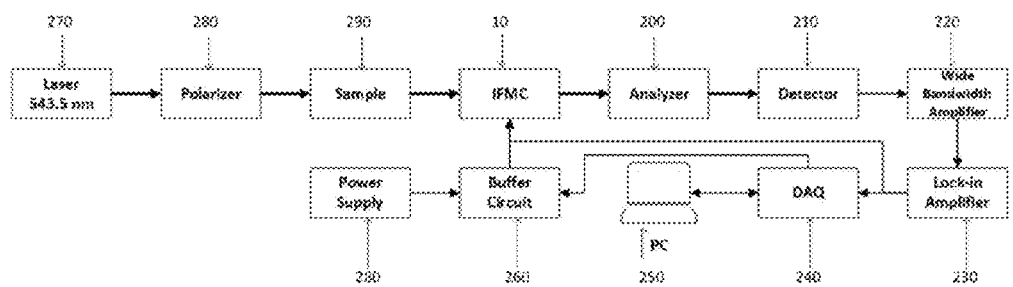
FIG. 15: Schematic illustration of a polarimetric glucose sensing system using an IFMC system. The thick lines represent the path of light, and the thin lines represent electrical communication.

In order to compare the IFMC system to other Faraday-based glucose detection systems, polarimetric measurements were taken in the hypoglycemic and hyperglycemic concentration ranges. Static validation of the IFMC system was carried out using a polarimetric system as depicted schematically in FIG. 15, with a 1 cm open-air sample cell 290 that allowed for liquid to be easily pipette into and out of the light path, contained between two glass microscope cover slides (Thermo Fisher Scientific, Waltham, Mass.). The modulated signal was monitored with the lock-in amplifier 230 which output a signal to the DAQ (NI USB-6212, National Instruments, Austin, Tex.) 240 and onto a PC 250. The information was processed in a PID continuous feedback virtual instrument (VI) created in LabVIEW (National Instruments, Austin, Tex.). The feedback loop controlled a voltage buffer circuit (LT1010, Linear Technology, Milpitas, Calif.) 260 powered with a DC power supply (Hewlett-Packard Company, Palo Alto, Calif.) 280 through the DAQ 240 which would apply a DC voltage to the compensator coil 24 in order to align the polarized signal perpendicularly to the analyzer by magnetic field generation, centering the modulated signal on the null plane and producing a $2\omega_m$ detected signal. This applied voltage was proportional to any rotation in the polarized signal that would occur within the system, such as that due to glucose within the sample cell. Therefore, the output from the PID controller could be directly used to predict the glucose concentration in unknown samples of fixed path length with a linear calibration model over a known range.

To begin, glucose solutions were prepared in 2 mL volumes using deionized (DI) water and a 1000 mg/dL glucose stock. The stock solution was created with a powder form of D-(+)-glucose (Sigma-Aldrich, St. Louis, Mo.) 24 hours prior to polarimetric testing in order to achieve complete mutarotation equilibrium. Standard dilutions were made in the hypoglycemic range from 0 to 100 mg/dL in intervals of 10 mg/dL as well as in the hyperglycemic range from 0 to 600 mg/dL in intervals of 50 mg/dL. The solutions were pipetted at random into the sample cell for each dilution range and the compensator voltage was noted. The sample cell was rinsed with DI water between measurements.

Two separate data sets were collected for both concentration ranges. Calibration models were formulated using least-squares linear regression for each concentration range after subtracting the baseline measurement. Then, the data was plotted and the errors of calibration and prediction were calculated in MATLAB (MathWorks, Natick, Mass.). The standard error of calibration (SEC) was calculated by evaluating the calibration data set and determining the standard deviation of the residuals against the expected values, as shown in Equation 17:

$$SEC = \sqrt{\frac{1}{(N-1)}\sum_{i=1}^{N}(C_i - \overline{C})^2}$$ Equation 17 where C is the set of residuals from the calibration data.

The standard error of prediction (SEP) was calculated in a similar fashion but by evaluating a separate data set, not used in calibration, according the following Equation 18:

$$SEP = \sqrt{\frac{1}{(N-1)}\sum_{i=1}^{N}(P_i - \overline{P})^2}$$ Equation 18 where P is the set of residuals from the prediction data. The residuals are the difference between the predicted and actual concentration.

Figure 19A:
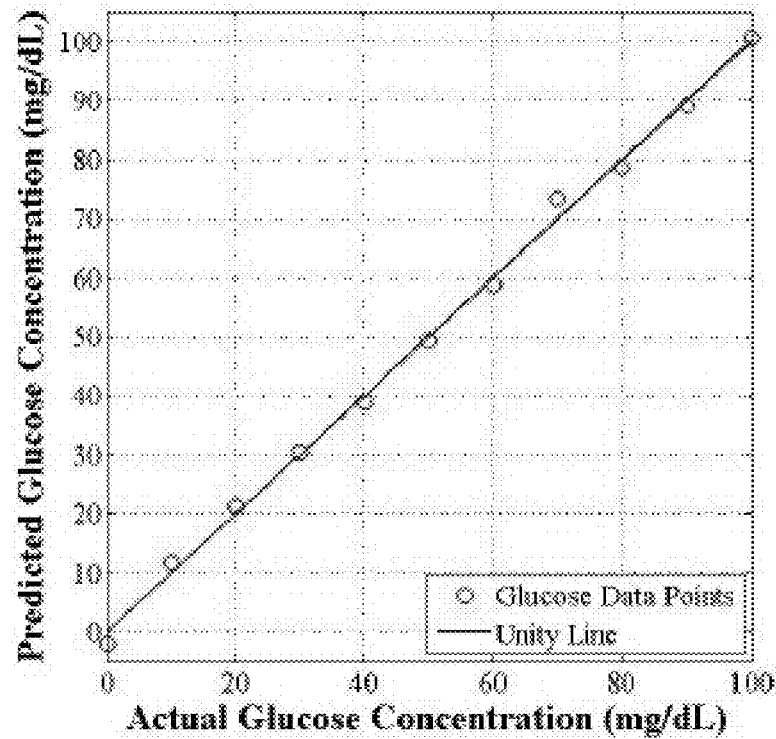
FIGS. 19A-19D: Graphs showing calibration and validation of hypoglycemic and hyperglycemic glucose detection.
Figure 19B:
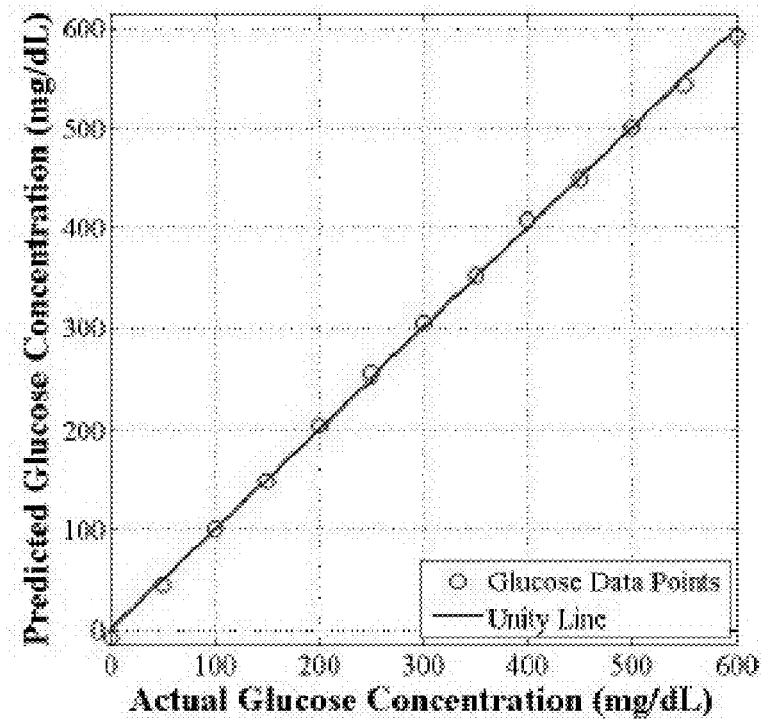
Figure 19C:
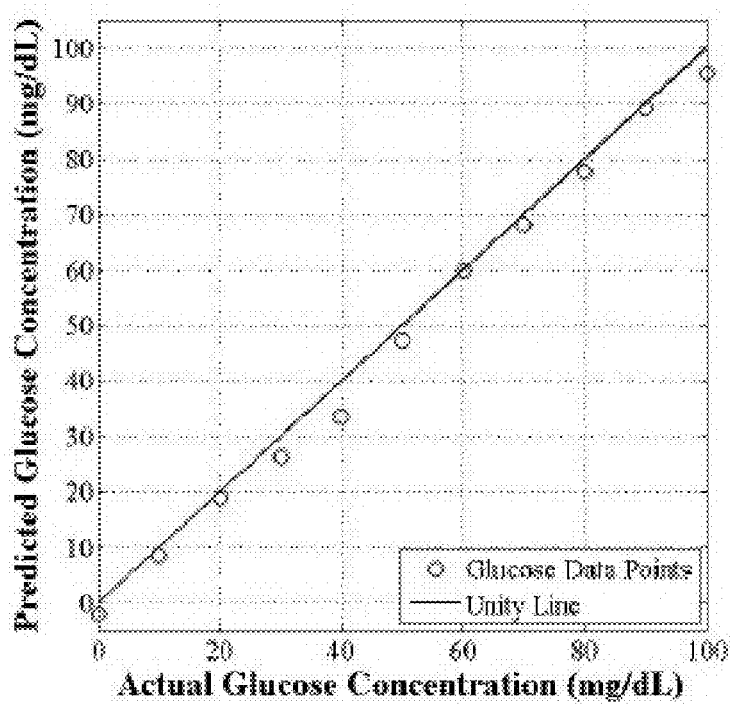
Figure 19D:
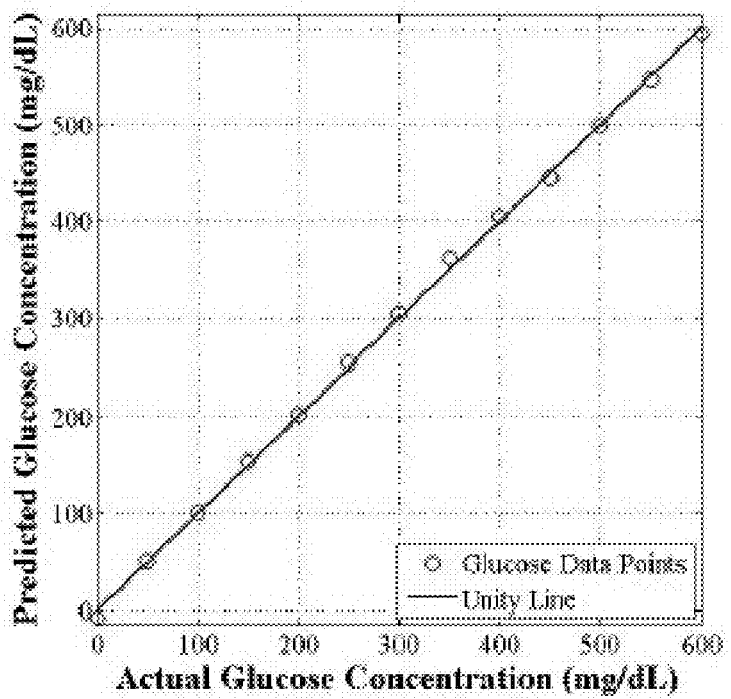

The calibration and prediction results for the hypoglycemic and hyperglycemic concentration ranges against the actual concentration values are shown by FIGS. 19A-19D, where the calibration results for hypoglycemic concentrations and hyperglycemic concentrations are shown in FIGS. 19A-19B, respectively, and the prediction results for hypoglycemic concentrations and hyperglycemic concentrations are shown in FIGS. 19C-19D, respectively. The hypoglycemic data resulted in a SEC of 1.6 mg/dL with an $R^2$ of 0.9977 and a SEP of 1.8 mg/dL with an $R^2$ of 0.9970. The hyperglycemic data resulted in a SEC of 5.2 mg/dL with an $R^2$ of 0.9993 and a SEP of 5.4 mg/dL with an $R^2$ of 0.9992. The main source of error within the system was due to the sensitivity required to measure sub-millidegree rotations. Although optical systems are capable of accurately detecting these measurements, electromagnetic noise and physical vibrations play a noticeable role in the overall capabilities of these systems. These results show that the IFMC system is capable of achieving measurement sensitivity with similar, if not better, accuracy than the larger, two-part modulator/compensator devices.

Flow System Validation

Figure 20:
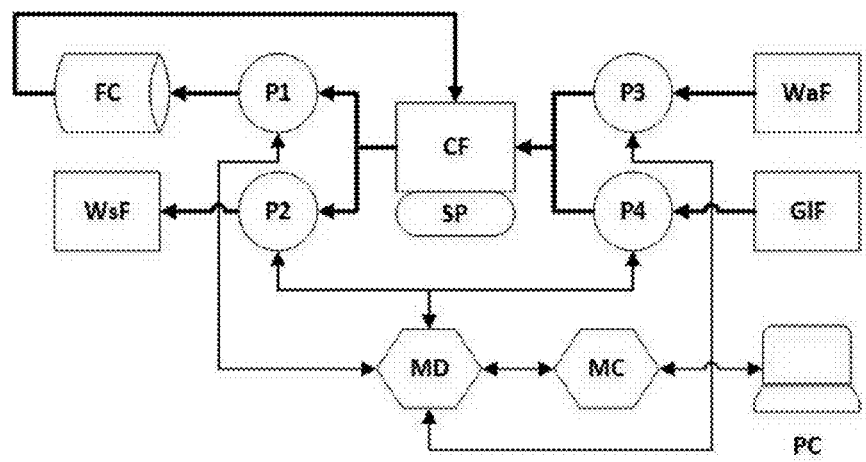
FIG. 20: Schematic illustration of a programmable flow system. In the schematic, thick lines represent the fluid path while thin lines correspond to electronic communication. The component labels are as follows: flow cell (FC), photodetector (PD), pump 1 (P1), pump 2 (P2), pump 3 (P3), pump 4 (P4), central flask (CF), waste flask (WsF), water flask (WaF), glucose flask (GlF), stir plate (SP), microcontroller (MC), and motor driver (MD). P3 is located behind P2, and P4 is located behind P1.

A flow system reproduces the physiological conditions experienced in animal models without the need for actual animal testing. A primary testing characteristic of in vivo systems is the capability to track physiological glucose profiles in real-time. A programmable glucose flow system capable of being integrated with the polarimeter PID control program was thus developed, providing real-time output as it corresponds to changing glucose concentrations. The programmable flow system was composed of four WPX1 peristaltic pumps with stepper motors (WELCO Co., Ltd., Tokyo, Japan) and all-purpose silicon Tygon tubing (Saint-Gobain S.A., Courbevoie, France). A schematic of the flow system coupled to the polarimeter is shown in FIG. 20.

Figure 21:
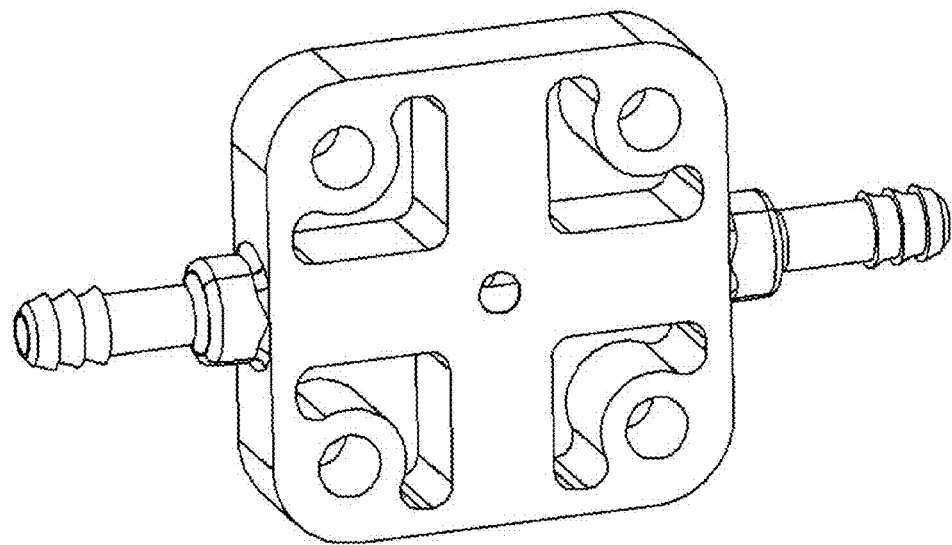
FIG. 21: Perspective view of a 1 cm flow cell capable of being mounted to a polarimeter for stable continuous measurements.

Pump 1 (WPX1-S3/16FA4-W4C-CP) was set up to run continuously to circulate glucose solutions from a well-mixed central flask, through a custom-designed and 3D-printed 1 cm flow cell that was sealed on either side with glass microscope cover slides, and back into the central flask for continuous mixing. One example of a custom-designed flow cell is shown in FIG. 21. Pump 2 (WPX1-S1/8FB4-W4C-YP) would remove waste from the central flask to maintain a constant liquid volume during concentration changes. Pump 3 (WPX1-S3/32FB4-WM4-BP) would add DI water to the central flask during a concentration decrease. Pump 4 (WPX1-S3/32FB4-WM4-GP) would add a 1000 mg/dL glucose stock solution to the central flask during a concentration increase.

The stepper motors on each pump were driven with a Quadstepper Motor Driver Board (SparkFun Electronics, Boulder, Colo.), which was controlled through an Arduino Mega 2560 R3 Microcontroller Board (Officine Arduino Torino, Torino, Italy). The microcontroller was programmed with a customized version of the open source LabVIEW Interface for Arduino toolkit (LIFA) through the Arduino development software which was capable of running the Quadstepper Motor Driver Board. Both the Arduino programming environment and the LIFA toolkit were downloaded as open source applications from the internet.

Three separate LabVIEW VIs were developed and integrated to the polarimeter PID VI for collecting real-time glucose measurement data based on the polarimeter response as related to actual concentration in the flow cell. The first VI was used to purge the tubing prior to each experiment in order to fill the lines with the corresponding solutions and remove air bubbles. The second VI was designed for changing glucose concentrations as the system was running for calibration and testing purposes. The third VI was used for programming predefined glucose profiles to run continuously over a designated period of time in order to mimic the physiological interactions between insulin and glucose. Each VI was designed with the appropriate fields for updating real-time concentration, monitoring or changing the stepper motor status, tracking flask concentration and volume, and visualizing the polarimetric output.

When the flow system was running, the central flask was maintained at a consistent 50 mL volume and continuously mixed on a magnetic stir plate (Corning, Tewksbury, Mass.). When the concentration was changed in the central flask, the waste pump would pull out the allotted volume of liquid prior to the addition of glucose stock or water in order to minimize equilibrium time. Also, the circulation pump utilized a minimal length of tubing, set to run at a flow rate of 51.187 mL/min. All concentration changes were spaced at two-minute intervals in order to allow adequate time for system equilibrium. Prior to initial use, each pump was calibrated using DI water and an analytical balance by weighing a sample dispensed from 10 rotations of the pump head and calculating a volume per rotation figure. This would allow for maximum accuracy over long periods of time when programmed into the flow system VI. It was determined that pumps 1, 2, 3, and 4 would dispense 0.910, 0.472, 0.337, and 0.336 mL per revolution of the pump head, respectively. These values were programmed into the flow system VI and standard glucose dilutions in the hypoglycemic and hyperglycemic range were created.

The system was then validated by mixing glucose solutions of known concentration using the flow system. The glucose concentration in the central flask was ramped up from 0 to 100 mg/dL in 10 mg/dL intervals and again from 0 to 600 mg/dL in 50 mg/dL intervals. After the concentration equilibrated with each change, 2 mL samples were removed and the flask volume within the LabVIEW VI was adjusted accordingly for correct concentration calculations. The samples were then compared to measurements taken with a YSI 2300 STAT Plus Glucose and Lactate Analyzer (YSI Life Sciences, Inc., Yellow Springs, Ohio) in triplicate, and the system error was calculated. The averaged data resulted in a standard error of 0.5 mg/dL in the hypoglycemic range and 6.4 mg/dL in the hyperglycemic range. These values were within the limits of the YSI, per the manufacturer's documentation. Given the precision control of the stepper motor-driven pump heads and the individual calibration of each head, the primary source of error was likely centered on the YSI rat her than the flow system. The flow system was proven to be capable of producing accurately-controlled real-time glucose solutions in order to facilitate robust continuous polarimetric measurements similar to standard in vivo experiments.

Continuous Dynamic Glucose Detection

Once the flow system was validated, the IFMC system was evaluated in a real-time dynamic system using the glucose flow system and a custom 1 cm flow cell. A different calibration model was created for the polarimeter with the custom flow cell and the IFMC system. This was done by averaging three collected data sets, less the baseline measurements, over a range of 0 to 200 mg/dL, and fitting the data to a least-squares linear regression model. This calibration model resulted in a SEC of 3.5 mg/dL with an $R^2$ of 0.9972, which is in similar agreement with the static glucose data.

Prior to running the 500-minute physiological glucose profile with the IFMC system, a new calibration model was formulated for the flow cell. This was done by averaging three collected data sets, less the baseline measurements, over a range of 0 to 200 mg/dL, and fitting the data to a least-squares linear regression model. 50 mL glucose solutions were made in DI water between 0 and 200 mg/dL in 20 mg/dL intervals. Each solution was purged through the flow cell at random while running the PID VI, and the voltage output to the polarimeter was noted. The flow cell was flushed with DI water between each measurement, and the baseline voltage was noted. This process was carried out in triplicate, and the baseline was subtracted from each data point. The data sets were averaged, and a final least-squares linear regression calibration model was formed. The new calibration model resulted in a SEC of 3.5 mg/dL with an $R^2$ of 0.9972, which is in similar agreement with the static glucose data. This model was then programmed into the PID VI so that continuous glucose measurements could be taken and monitored through the flow system VI to track a physiological concentration profile over time.

The glucose profile used for continuous monitoring was calculated with a mathematical model that simulates the human ultradian oscillations of insulin and glucose. The six-state differential system was solved using XPPAUT, an open source numerical integration software package. The final profile reflects the glucose response in a non-diabetic person following a 50 g oral glucose tolerance test (OGTT) beginning with fasting glucose and insulin levels using the gastrointestinal absorption rate equation as the glucose input parameter. The profile data was exported to MATLAB and saved as a two-column text file containing time in two-minute intervals for a duration of 500 minutes (beginning with t=2 min) and the corresponding glucose concentrations in mg/dL. The data was then uploaded into the flow system profile VI which would update the glucose concentration in the central flask every two minutes, producing a continuous physiological profile for the polarimeter to monitor through the flow cell.

Prior to beginning the 500-minute continuous glucose monitor experiment, 50 mL of DI water was added to the central flask and purged through the flow cell so that no air bubbles remained in the circulation path. With the circulation pump and stir plate running, the polarimeter was turned on and the initial baseline measurement was set in the calibration model within the PID VI. Then, the concentration in the central flask was brought to an initial 80 mg/dL and the flow system profile VI was started at t=0 min. The polarimeter output was plotted in real-time at a frequency of 1 Hz along with the actual concentration in the central flask. After the 500-minute testing period, the system was shut down and the final data set containing the polarimeter output was exported and saved. The data was then imported into MATLAB where it was plotted and the errors for continuous measurements over time were calculated. The same continuous test was repeated two more times for a total of three data sets.

Figure 22:
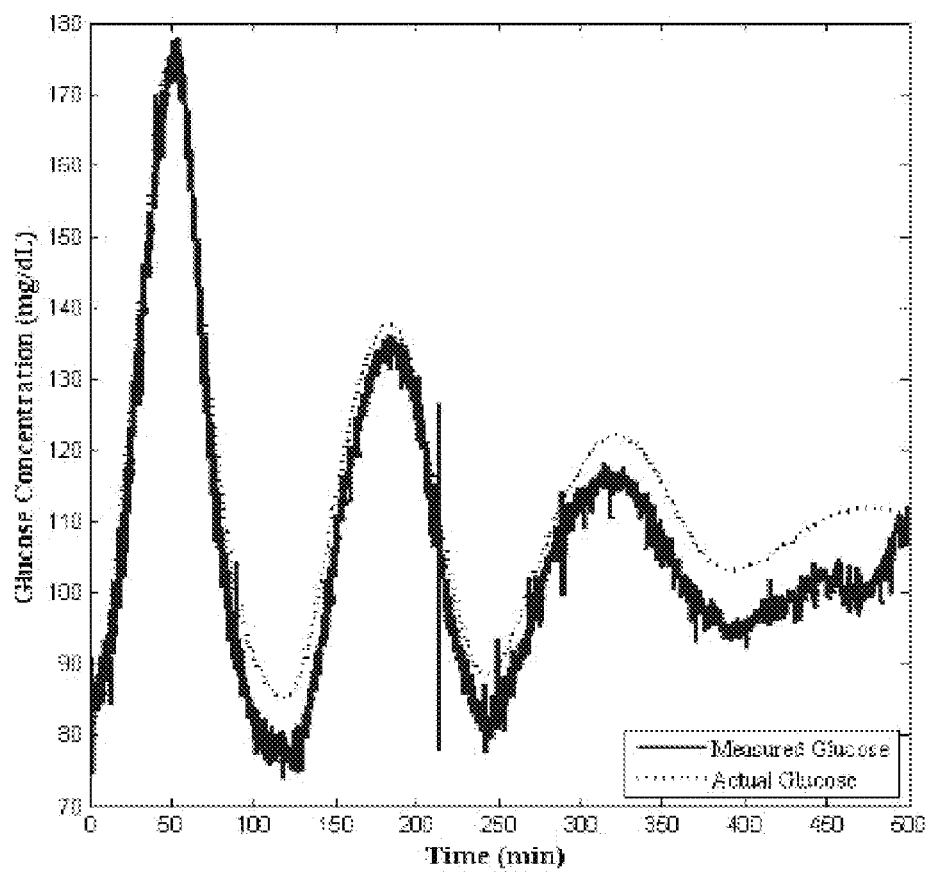
FIG. 22: Graph of glucose concentration (mg/dL) versus time (min), showing a 500-minute continuous polarimetric glucose detection test as measured with the IFMC system. The data is plotted against the actual physiological glucose profile used during the test.

The raw data results of the continuous polarimeter output are shown in FIG. 22, as compared to the actual real-time glucose concentration in the central flask. As shown in FIG. 22, the polarimeter tracked the overall profile with precision. However, as time went on, the output signal drifted with respect to the actual profile. In order to quantify the error over time, the SEP was calculated at 100-minute intervals using the raw data. The SEPs during the first 100, 200, 300, 400, and 500 minutes were determined to be 4.3, 3.7, 3.2, 3.1, and 3.2 mg/dL, respectively. Based on these results, the system is capable of tracking concentration changes with a precision that is consistent with the calibration model. The calibration model remains valid, but the baseline shifted. In order to quantify the baseline drift, the mean of the residuals was also calculated over the same 100-minute intervals to be 4.2, 5.3, 5.2, 5.7, and 6.2 mg/dL, respectively. These results show a consistent decrease in system accuracy as drift occurs over time. The cause for the drift is explained due to the physical sensitivity of the system. Although the optical components were mounted on an optical table and supported with 30 mm cage mounts, the slightest table movement can lead to spikes in the system output (as shown around the 210-minute mark in FIG. 22). This coupled with consistent vibration of the driving electronics, the stir plate, and the peristaltic pumps on the table can cause the position of each component in the system to slightly shift over time, resulting in a change in the polarization state of the signal. Furthermore, the branching off of the data during the last 20 minutes of the experiment was caused by an air bubble that became trapped in the flow cell. Air bubbles can be minimized or eliminated by alternate designs for the interior volume of the flow cell.

A final analysis on the data was conducted to realign the baseline every 20 minutes to the calibration model before running a 60-second moving average. This type of baseline correction can be rationalized due to the nature of the final system that is to be used by diabetics. Continuous measurements are preferred for achieving accurate results. However, a hand-held glucose meter would be used by patients on the order of a few minutes, meaning that baseline measurements can be taken before and after each reading. Applications that require long-term monitoring, such as use with sugar monitoring in cell culture bioreactors, can be designed to implement single-point baseline corrections, which are common for many commercial glucose meters such as the YSI.

Figure 23:
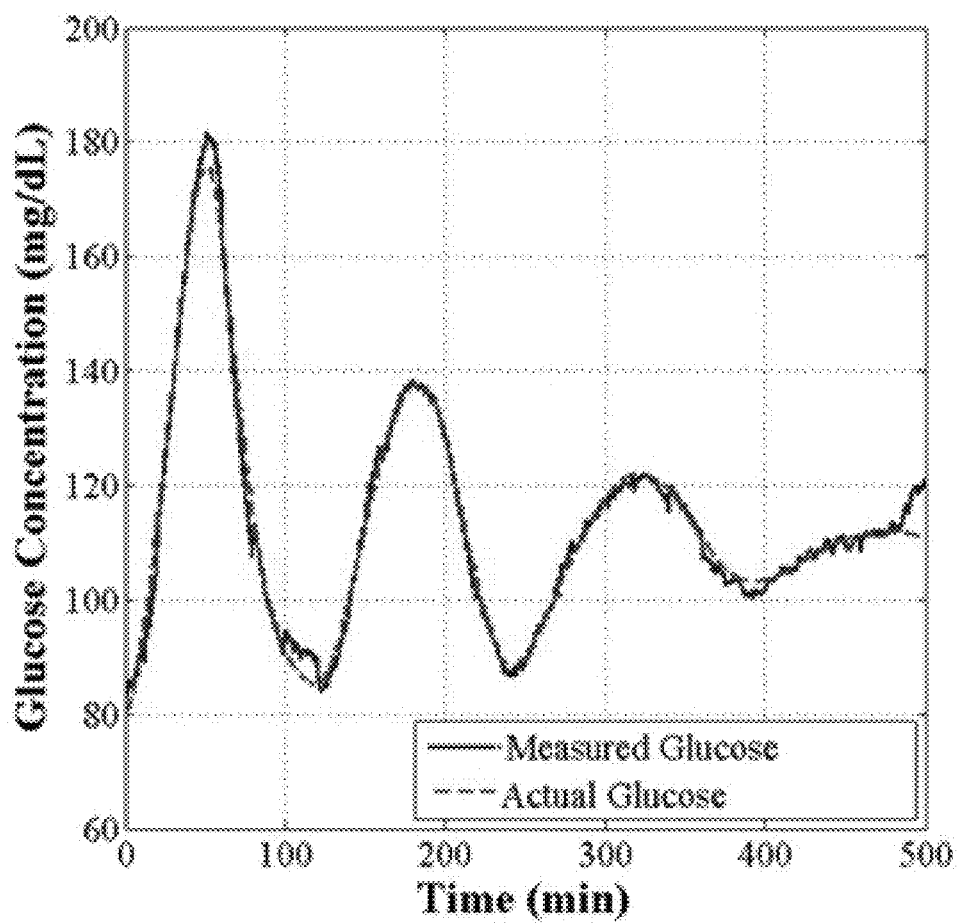
FIG. 23: Graph of glucose concentration (mg/dL) versus time (min) for a first test, showing a 20-minute baseline-corrected, 60-second moving-averaged data profile of the data shown in FIG. 22. The data is plotted against the actual physiological glucose profile used during the test.

The baseline-corrected results, shown in FIG. 23, demonstrate a much better fit to the actual concentration profile. It should be noted that the system was not recalibrated as the model was still valid based on the SEP, but rather the baseline was shifted accordingly and the excessive noise was masked. The branching off of the data in the last 20 minutes of the experiment was caused by an air bubble that became trapped in the flow cell. Problems such as these could be minimized by redesigning the interior volume of the flow cell. Air bubbles are primarily an issue with sample cell design, and therefore would not be a problem during actual physiological sensing. The final baseline corrected SEP was calculated to be 3.5 mg/dL with the overall mean of the residuals to be 0.2 mg/dL. These results indicate that the baseline-corrected data maintains similar error to the calibration model as well as to the raw data while the drift is negated.

Figure 24:
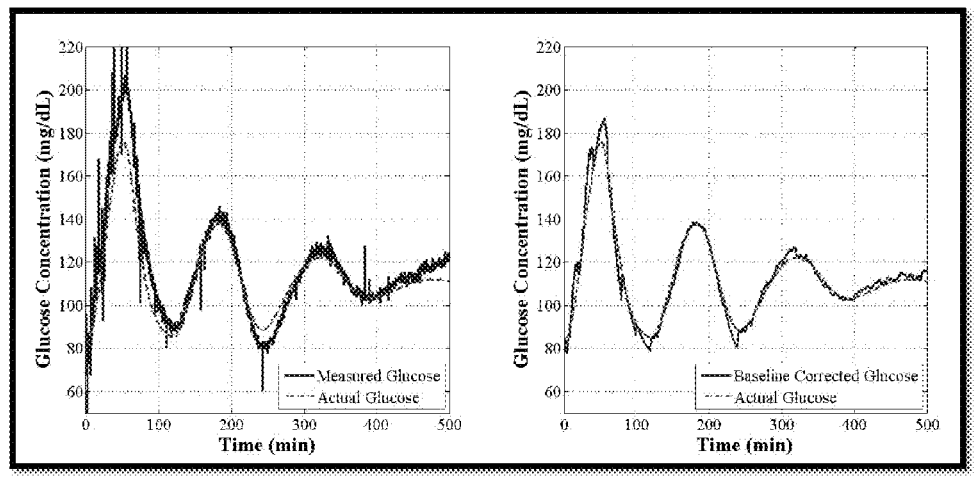
FIG. 24: Graph of glucose concentration (mg/dL) versus time (min) for a second test, showing a 500-minute continuous polarimetric glucose detection test as measured with the IFMC system (left), and the 20-minute baseline correct, 60-second moving averaged data profile (right). Both data sets are plotted against the actual physiological glucose profile used during the test.
Figure 25:
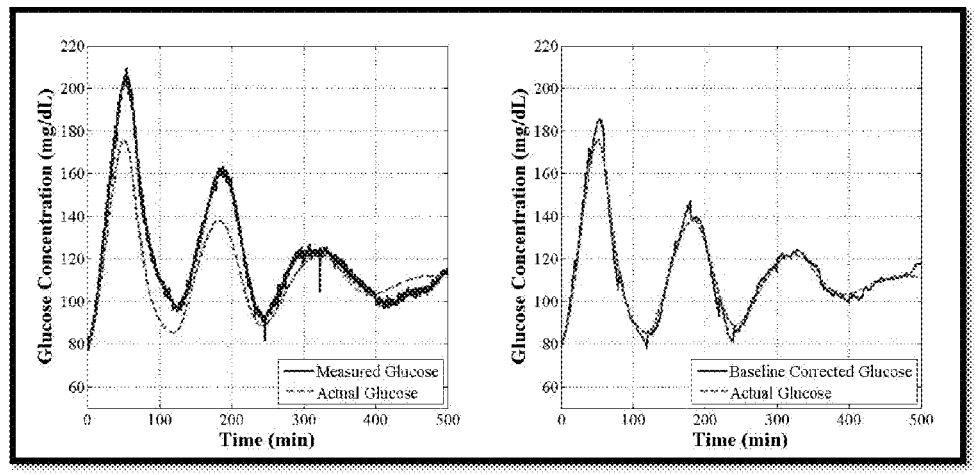
FIG. 25: Graph of glucose concentration (mg/dL) versus time (min) for a third test, showing a 500-minute continuous polarimetric glucose detection test as measured with the IFMC system (left), and the 20-minute baseline corrected, 60-second moving averaged data profile (right). Both data sets are plotted against the actual physiological glucose profile used during the test.

The real-time test was repeated two more times, and the results are shown in FIGS. 24-25. Both of these plots display various baseline drift over time due to vibrational effects, similar to the initial results, further indicating the overall sensitivity of the polarimetric system. The second trial resulted in an overall SEP of 7.9 mg/dL from the raw data, and a SEP of 4.2 mg/dL after performing the same baseline correction and moving average. The third trial resulted in an overall SEP of 10.3 mg/dL from the raw data, and a SEP of 3.6 mg/dL after baseline correction. Therefore, the results are repeatable and a single-point baseline correction can be used to realign any vibrational baseline drift.

Figure 26:
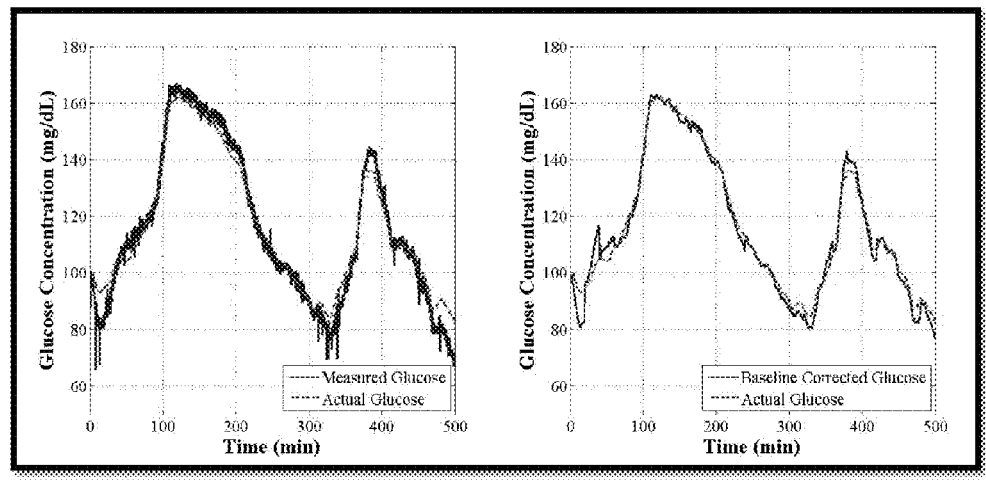
FIG. 26: Graph of glucose concentration (mg/dL) versus time (min) for a fourth test, showing a 500-minute continuous polarimetric glucose detection test using a clinical diabetic profile as measured with the IFMC system (left), and a 20-minute baseline corrected, 60-second moving averaged data profile (right). Both data sets are plotted against the actual physiological glucose profile used during the test.
Figure 27:
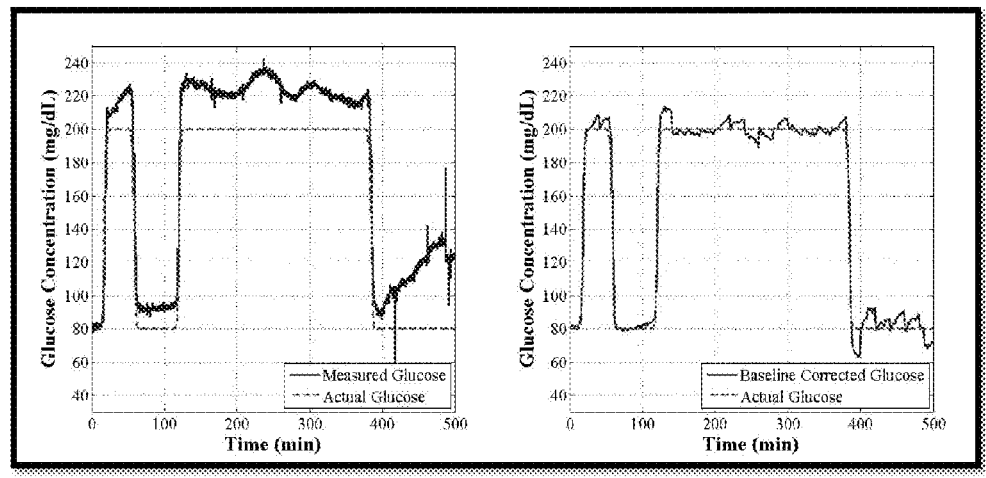
FIG. 27: Graph of glucose concentration (mg/dL) versus time (min) for a fifth test, showing a 500-minute continuous polarimetric glucose detection test using a near-step change profile as measured with the IFMC system (left), and a 20-minute baseline corrected, 60-second moving averaged data profile (right). Both data sets are plotted against the actual physiological glucose profile used during the test.

After determining the IFMC system can successfully track a non-diabetic physiological glucose profile over time based on a controllable mathematical model, the test was repeated with two different profiles. First, the system was tested against a clinical profile from a patient with type 1 diabetes, providing information following meal ingestion and insulin injections. Then, the limitations of the flow system and IFMC system were tested against a near-step change profile with a maximum rate of change in concentration of 27.5 mg/dL/min and an average change of 10 mg/dL/min. The results from these additional experiments are displayed in FIGS. 26-27, respectively.

The diabetic profile resulted in an overall SEP of 4.8 mg/dL, with a baseline-corrected SEP of 3.4 mg/dL. The near-step profile resulted in an overall SEP of 11.1 mg/dL, with a baseline-corrected SEP of 5.4 mg/dL. The diabetic profile demonstrated good tracking, even in the raw data, while the step profile showed a variable amount of baseline drift. The SEP encountered from the raw data is variable, depending on the overall amount of drift. However, the single-point baseline corrected data provides a better representation of the system, with an average SEP of 3.8 mg/dL from all data sets. This indicates that the relative amount of drift that occurs in the system is situational, and the single-point baseline correction can successfully combat this issue. Furthermore, these results demonstrate that the IFMC system can successfully track a clinical diabetic profile during normal conditions as well as during the worst-case conditions, which are represented by the high rate of change seen in the near-step change profile. Regardless of the drift, the results show that the IFMC system is capable of achieving the necessary rotational sensitivity and stability required for continuous physiological glucose detection.

Overall, these results demonstrate that the IFMC system can perform similar to, if not better than, the larger two-part modulator/compensators. The IFMC system is thus a useful component for noninvasive polarimetric glucose detectors. This device is beneficial in personalized glucose monitors for diabetic patients because it consolidates size and cost requirements and can achieve the same effect as its two-part predecessors. The examples show not only that the IFMC system meets the minimum design requirements for physiological detection, but also that it maintains a degree of sensitivity similar to, if not better than, previously tested configurations with overall SEPs of 1.8 mg/dL and 5.4 mg/dL in the hypoglycemic and hyperglycemic concentration ranges, respectively.

Certain embodiments of the devices and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. An integrated Faraday modulator/compensator (IFMC) system comprising:
    an optical material;
    at least one AC magnetic field source disposed in a first position in proximity to the optical material, the AC magnetic field source being configured to generate a first magnetic field; and,
    at least one DC magnetic field source disposed in a second position in proximity to the optical material, the DC magnetic field source being configured to generate a second magnetic field;
    the first position and the second position being configured to cause the first magnetic field and the second magnetic field to be superimposed on the optical material.

2. The IFMC system of claim 1, wherein the optical material comprises a single optical crystal.

3. The IFMC system of claim 1, wherein superposition of the first and second magnetic fields within the optical material causes rotational modulation and compensation of a light beam's electric field passing through the optical material.

4. The IFMC system of claim 1, wherein the optical material is aligned on a first axis, the at least one AC magnetic field source is aligned on a second axis, and the at least one DC magnetic field source is aligned on a third axis; wherein the first, second, and third axes are in a parallel, and spaced-apart, alignment.

5. The IFMC system of claim 1, wherein one or more spaces are defined between the optical material and the AC magnetic field source or the DC magnetic field source.

6. The IFMC system of claim 1, wherein orientation of at least one of the first magnetic field and the second magnetic field is adjustable with respect to the each other and to the optical material.

7. The IFMC system of claim 1, wherein each of the AC and DC magnetic field sources is comprised of an inductive coil circumferentially surrounding a ferromagnetic core; and,
    wherein the magnitude of the first magnetic field and the second magnetic field is dependent on the distance from each AC magnetic field source and DC magnetic field source as well as the magnitude of a current driving each inductive coil, while the direction of each magnetic field is perpendicular to a plane formed by the intersection of the current and separation vectors using Equation 4:

$$B(r) = \frac{\mu_0}{4\pi} \oint \frac{I \times R}{R^3} dr_0;$$

wherein bolded terms represent vector quantities, B(r) is the magnetic field at any point in space a distance r from the origin, $\mu_0$ is the permeability of free space ($4\pi \times 10^{-2}$ N/A$^2$), I is the current, R is the vector directed from the source point to r, and $dr_0$ is an element of length along the current path.

8. The IFMC system of claim 1, wherein the first magnetic field is generated by an AC current from a first power source, and the second magnetic field is generated by a DC current from a second power source.

9. The IFMC system of claim 1, wherein each of the AC and DC magnetic field sources is comprised of an inductive coil circumferentially surrounding a ferromagnetic core; wherein each the ferromagnetic cores defines an axis that is parallel to, and annularly spaced at about 90° intervals around, an axis defined by the optical material.

10. The IFMC system of claim 1, wherein the IFMC system has a modulation depth of about 1° and a maximum compensation depth of about 0.0632°.

11. The IFMC system of claim 1, wherein the AC magnetic field source comprises a high-powered resonant circuit having one or more inductive coils and a magnetic core.

12. The IFMC system of claim 1, wherein the AC magnetic field source comprises a ferromagnetic core and an electrically driven coil.

13. The IFMC system of claim 12, wherein different size, shape, and/or inductances of the coil provides a desire operational range of rotations based on the maximum voltage supplied to the AC magnetic field source.

14. The IFMC system of claim 1, wherein the AC magnetic field source comprises a vibrationally mounted permanent magnet.

15. The IFMC system of claim 1, wherein the AC magnetic field source comprises at least one 100 mH inductor.

16. The IFMC system of claim 1, wherein the DC magnetic field source is comprised of a low-powered DC circuit having one or more inductive coils and a magnetic core.

17. The IFMC system of claim 1, wherein the DC magnetic field source comprises a ferromagnetic core and an electrically driven coil.

18. The IFMC system of claim 17, wherein different size, shape, and/or inductances of the coil provides a desire operational range of rotations based on the maximum voltage supplied to the DC magnetic field source.

19. The IFMC system of claim 1, wherein two or more AC magnetic field sources are connected in series such that current flows in the same direction around each coil, producing a collectively maximized axial component of the magnetic field along the optical material, and achieving an effective Faraday modulation to light passing through the optical material.

20. The IFMC system of claim 1, wherein the optical material comprises a terbium-doped glass (TDG) material; a terbium gallium garnet (TGG) material; or, an yttrium iron garnet (YIG) material.

21. The IFMC system of claim 1, wherein the optical material has a length-to-diameter aspect ratio of about 2.5.

22. The IFMC system of claim 1, wherein the optical material has a length of about 13.5 mm and a diameter of about 5.4 mm.

23. The (IFMC) component apparatus of claim 1, wherein
the first power source is disposed outside a modular housing and configured to supply an AC current to the AC magnetic field source; and,
the second power source disposed outside the modular housing and configured to supply a DC current to the DC magnetic field source.

24. The IFMC component apparatus of claim 23, further including a polarizer disposed outside the modular housing and configured to supply polarized light through the optical material.

25. The IFMC component apparatus of claim 23, further including an analyzer disposed outside the modular housing and configured to receive modulated and compensate light from the IFMC system.

26. The IFMC component apparatus of claim 23, further including a detector disposed outside the modular housing and configured to receive modulated and compensate light from the analyzer.

27. The IFMC component apparatus of claim 23, further including a feedback signaling system disposed outside the modular housing and configured to receive modulated and compensate light from the detector and configured to provide a feedback signal to at least one DC magnetic field source.

* * * * *